United States Patent [19]
Wnendt et al.

[11] Patent Number: 5,976,841
[45] Date of Patent: Nov. 2, 1999

[54] PROTEINS HAVING FIBRINOLYTIC AND COAGULATION—INHIBITING PROPERTIES

[75] Inventors: Stephan Wnendt, Aachen; Regina Heinzel-Wieland, Darmstadt; Gerd Josef Steffens, Aachen, all of Germany

[73] Assignee: Gruenenthal GmbH, Aachen, Germany

[21] Appl. No.: 08/560,098

[22] Filed: Nov. 17, 1995

[30] Foreign Application Priority Data

Nov. 17, 1994 [DE] Germany .............................. 44 40 892

[51] Int. Cl.⁶ .............................. C12N 9/72; C12N 15/58; C12N 15/62; A61K 37/00
[52] U.S. Cl. ...................... 435/69.7; 435/226; 435/252.3; 435/252.33; 435/320.1; 435/471; 424/94.64; 536/23.2; 536/23.4; 935/14; 935/29; 935/47; 935/73
[58] Field of Search .................................. 435/69.7, 212, 435/252.3, 252.33, 320.1; 536/23.4; 424/94.64

[56] References Cited

U.S. PATENT DOCUMENTS

| | | | |
|---|---|---|---|
| 4,751,180 | 6/1988 | Cousens et al. | 435/69.7 |
| 4,944,943 | 7/1990 | Eschenfelder et al. | 424/94.64 |
| 5,002,887 | 3/1991 | Larsen | 435/212 |

(List continued on next page.)

FOREIGN PATENT DOCUMENTS

| | | |
|---|---|---|
| 0 328 957 | 8/1989 | European Pat. Off. . |
| 0 365 468 | 4/1990 | European Pat. Off. . |
| WO 91/09125 | 6/1991 | European Pat. Off. . |
| 41 37 996 | 5/1993 | Germany . |
| WO 86/03517 | 6/1986 | WIPO . |
| WO 89/10402 | 11/1989 | WIPO . |
| WO 91/01142 | 2/1991 | WIPO . |
| WO 92/01712 | 2/1992 | WIPO . |
| WO 92/10575 | 6/1992 | WIPO . |
| WO 92/14750 | 9/1992 | WIPO . |
| WO 92/18319 | 10/1992 | WIPO . |

OTHER PUBLICATIONS

Sako, T., et al., Molecular and General Genetics, vol. 190, "Cloning and expression of the staphylokinase gene of *Staphylococcus aureus* in *Escherichia coli*", pp. 271–277, 1983.

Harvey, P. P., et al., Proceedings of the National Academy of Sciences, U.S.A., vol. 83, "Cloning and expression of a cDNA coding for the anticoagulant hirudin from the blood-sucking leech, *Hirudo medicinalis*", pp. 1084–1088, 1986.

(List continued on next page.)

*Primary Examiner*—Robert A. Wax
*Assistant Examiner*—William W. Moore
*Attorney, Agent, or Firm*—Evenson, McKeown, Edwards & Lenahan, P.L.L.C.

[57] ABSTRACT

Proteins having fibrinolytic and coagulation-inhibiting properties which are linked at the N- and/or C-terminal end of the plasminogen-activating amino acid sequence to a thrombin- or factor Xa-inhibiting amino acid sequence. The proteins, which are produced by genetic engineering, are useful as thrombolytic agents.

8 Claims, 21 Drawing Sheets

Met-Ser-Asn-Glu-Leu-Asp-Pro-Arg-Pro-Phe-Leu-Leu-Arg-Asn-
Pro-Asn-Asp-Lys-Tyr-Glu-Pro-Phe-Trp-Glu-Asp-Glu-Glu-Lys-
Gly-Pro-His-Met-Ser-Ser-Pro-Pro-Glu-Glu-Leu-Lys-Phe-Gln-
Cys-Gly-Gln-Lys-Thr-Leu-Arg-Pro-Arg-Phe-Lys-Ile-Ile-Gly-
Gly-Glu-Phe-Thr-Thr-Ile-Glu-Asn-Gln-Pro-Trp-Phe-Ala-Ala-
Ile-Tyr-Arg-Arg-His-Arg-Gly-Gly-Ser-Val-Thr-Tyr-Val-Cys-
Gly-Gly-Ser-Leu-Ile-Ser-Pro-Cys-Trp-Val-Ile-Ser-Ala-Thr-
His-Cys-Phe-Ile-Asp-Tyr-Pro-Lys-Lys-Glu-Asp-Tyr-Ile-Val-
Tyr-Leu-Gly-Arg-Ser-Arg-Leu-Asn-Ser-Asn-Thr-Gln-Gly-Glu-
Met-Lys-Phe-Glu-Val-Glu-Asn-Leu-Ile-Leu-His-Lys-Asp-Tyr-
Ser-Ala-Asp-Thr-Leu-Ala-His-His-Asn-Asp-Ile-Ala-Leu-Leu-
Lys-Ile-Arg-Ser-Lys-Glu-Gly-Arg-Cys-Ala-Gln-Pro-Ser-Arg-
Thr-Ile-Gln-Thr-Ile-Cys-Leu-Pro-Ser-Met-Tyr-Asn-Asp-Pro-
Gln-Phe-Gly-Thr-Ser-Cys-Glu-Ile-Thr-Gly-Phe-Gly-Lys-Glu-
Asn-Ser-Thr-Asp-Tyr-Leu-Tyr-Pro-Glu-Gln-Leu-Lys-Met-Thr-
Val-Val-Lys-Leu-Ile-Ser-His-Arg-Glu-Cys-Gln-Gln-Pro-His-
Tyr-Tyr-Gly-Ser-Glu-Val-Thr-Thr-Lys-Met-Leu-Cys-Ala-Ala-
Asp-Pro-Gln-Trp-Lys-Thr-Asp-Ser-Cys-Gln-Gly-Asp-Ser-Gly-
Gly-Pro-Leu-Val-Cys-Ser-Leu-Gln-Gly-Arg-Met-Thr-Leu-Thr-
Gly-Ile-Val-Ser-Trp-Gly-Arg-Gly-Cys-Ala-Leu-Lys-Asp-Lys-
Pro-Gly-Val-Tyr-Thr-Arg-Val-Ser-His-Phe-Leu-Pro-Trp-Ile-
Arg-Ser-His-Thr-Lys-Glu-Glu-Asn-Gly-Leu-Ala-Leu-Ser-Pro-
Val-Lys-Ala-Phe-Pro-Arg-Pro-Gly-Gly-Gly-Gly-Asn-Gly-Asp-
Phe-Glu-Glu-Ile-Pro-Glu-Glu-Tyr-Leu (SEQ ID NO:46)

U.S. PATENT DOCUMENTS

| | | | |
|---|---|---|---|
| 5,126,134 | 6/1992 | Heim et al. | 424/94.64 |
| 5,182,113 | 1/1993 | Rigbi et al. | 424/537 |
| 5,187,098 | 2/1993 | Malke et al. | 435/320.1 |
| 5,188,829 | 2/1993 | Kobayashi et al. | 424/94.63 |
| 5,189,019 | 2/1993 | Palladino et al. | 514/12 |
| 5,194,589 | 3/1993 | Bott | 530/350 |
| 5,204,255 | 4/1993 | Tagawa et al. | 435/215 |
| 5,242,810 | 9/1993 | Maraganore et al. | 435/69.2 |
| 5,242,919 | 9/1993 | Rajput et al. | 435/359 |
| 5,256,770 | 10/1993 | Glaser et al. | 530/381 |
| 5,268,296 | 12/1993 | Maschler et al. | 435/252.3 |
| 5,328,898 | 7/1994 | Greenberg | 514/12 |
| 5,376,367 | 12/1994 | Williams | 424/85.2 |
| 5,434,073 | 7/1995 | Dawson et al. | 435/216 |
| 5,571,708 | 11/1996 | Yang et al. | 435/215 |
| 5,637,503 | 6/1997 | Brigelius-Flohe et al. | 435/320.1 |
| 5,648,250 | 7/1997 | Niwa et al. | 424/94.64 |
| 5,681,721 | 10/1997 | Steffens et al. | 435/69.6 |
| 5,747,291 | 5/1998 | Steffens et al. | 435/69.6 |
| 5,801,017 | 9/1998 | Werber et al. | 435/69.2 |

OTHER PUBLICATIONS

Maraganore, J. M., et al., The Journal of Biological Chemistry, vol. 264, "Anticoagulant activity of synthetic hirudin peptides", pp. 8692–8698, 1989.

Han, J. H., et al., Gene, vol. 75, "Cloning and expression of cDNA encoding antistasin, a leech–derived protein having anti–coagulant and anti–metastatic properties", pp. 47–57, 1989.

Gardell, S. J., et al., The Journal of Biological Chemistry, vol. 264, "Isolation, characterization, and cDNA cloning of a vampire bat salivary plasminogen activator", pp. 17947–17952, 1989.

Krstenansky, J. L., et al., FEBS Letters, vol. 269, "The C–terminal binding domain of hirullin P18. Antithrombin activity and comparison to other hirudin peptides", pp. 425–429, 1990.

Neeper, M. P., et al., The Journal of Biological Chemistry, vol. 265, "Characterization of recombinant tick anti–coagulant peptide. A highly–selective inhibitor of blood coagulation factor Xa", pp. 17746–17752, 1990.

Vu, T.-K. H., et al., Cell, vol. 64, "Molecular cloning of a functional thrombin receptor reveals a novel proteolytic mechanism of receptor activation", pp. 1057–1068, 1991.

Gardell, S. J., et al., Circulation, vol. 84, "Effective thrombolysis without marked plasminemia after bolus intravenous administration of vampire bat salivary plasminogen activator in rabbits", pp. 244–253, 1991.

Vu, T.-H. K., et al., Nature, vol. 353, "Domains specifying thrombin–receptor interaction", pp. 674–677, 1991.

Brigelius–Flohe, R., et al., Applied Microbiology and Biotechnology, vol. 36, "High expression vectors for the production of recombinant single–chain urinary plasminogen activator", pp. 640–649, 1992.

Yue, S.-Y., et al., Protein Engineering, vol. 5, "Characterization of the interactions of a bifunctional inhibitor with alpha–thrombin by molecular modeling and peptide synthesis", pp. 77–85, 1992.

Strube, K.-H., et al., The Journal of Biological Chemistry, vol. 268, "Isolation, sequence analysis, and cloning of haemadin", pp. 8590–8595, 1993.

Vlasuk, G. P., Thrombosis and Haemostasis, vol. 70, "Structural and functional characterization of tick anticoagulant peptide (TAP): A potent and selective inhibitor of blood coagulation factor Xa", pp. 212–216, 1993.

T.C. Wun et al., Journal of Biological Chemistry, vol. 257, "Isolation and characterization of urokinase from human plasma" pp. 3276–3283 1982.

H. Heyneker et al., Genetics of Industrial Microorganisms, "Functional expression of the human urokinase gene in E. coli", pp. 214–221 1982.

H. Lijnen et al., Journal of Biological Chemistry, vol. 261, "Activation of plasminogen by pro–urokinase", pp. 1253–1258 1986.

J. Maraganore et al., Biochemistry, vol. 29, "Design and characterization of hirulogs" pp. 7095–7101 1990.

D. Stump et al., Journal of Biological Chemistry, vol. 261, "Urokinase–related proteins in human urine", pp. 1267–1269 1986.

J. Krstenansky et al., Journal of Medicinal Chemistry, vol. 30, "Anticoagulant peptides", pp. 1688–1691 1987.

T. Rydel et al., Science, "The structure of a complex of recombinant hirudin and human alpha–thrombin", pp. 227–280 1990.

J. Robinson et al., Tibtech, vol. 9, "Redesigning t–PA for improved thrombolytic therapy", pp. 86–90 1991.

J. Schneider, Thrombosis Research, vol. 64, "Heparin and the thrombin inhibitor", pp. 677–687 1991.

H. Lu et al., Blood, vol. 78, Comparative thrombolytic properties of bolus injectins and continuous infusions of a chimeric anticoagulant, pp. 125–131 1991.

D. Collen et al., Blood, vol. 78, "Basic and clinical aspects of fibrinolysis and thrombolysis", pp. 3114–3124 1991.

H.R. Lijnen et al., Thrombosis and Haemostasis, vol. 66, "Strategies for the improvement of thrombolytic agents", pp. 88–110 1991.

N. Fromage et al., Fibrinolysis, vol. 5, "Synthesis purification and biological properties of a truncated mutant form of human tissue plasminogen activator produced in E. coli", pp. 187–190 1991.

A. Gruber et al., Circulation, vol. 84, "Antithrombotic effects of combining activated protein C and urokinase in nonhuman primates", pp. 2454–2462 1991.

S.K. Yao et al., Journal of the American Physiological Society, "Thrombin inhibition enhances tissue–type plasminogen", pp. 374–379 1992.

A. Szczeklik et al., Arteriosclerosis nd Thrombosis, vol. 12, "Persistent generation of thrombin after acute myocardial infarction", pp. 548–553 1992.

M. Mellott et al., Arteriosclerosis and Thrombosis, vol. 12, "Vampire bat salivary plasminogen activator", pp. 212–221 1992.

Gardell et al., "Isolation, Characterization, and cDNA Cloning of a Vampire Bat Salivary Plasminogen Activator", *The Journal of Biological Chemistry*, vol. 264, No. 30, Oct. 25, 1989, pp. 17947–17952.

Collen et al., "Thrombolytic and Pharmacokinetic Properties of Human Tissue–Type Plasminogen Activator Variants, Obtained by Deletion and/or Duplication of Structural/Functional Domains, in a Hamster Pulmonary Embolism Model", *Thrombosis and Haemostasis*, F.K. Schauttauer Verlagsgesellschaft mbH, Stuttgart, 65 (2) pp. 174–180, 1991.

Steffens et al., "The Complete Amino Acid Sequence of Low Molecular Mass Urokinase from Human Urine", *Hoppe-–Seyler's Z. Physical Chemistry*, BD. 363, S. 1043–1058, Sep. 1982.

Guenzler et al., "The Primary Structure of High Molecular Mass Urokinase from Human Urine: The Complete Amino Acid Sequence of the A Chain", *Hoppe–Seyler's Z. Physical Chemistry*, BD. 363, S. 1155–1165, Sep. 1982.

DIGESTION WITH BamHI AND NdeI,
ISOLATION OF THE LARGE RESTRICTION FRAGMENT,
DEPHOSPHORYLATION OF THE 5' ENDS,
LIGATION WITH SYNTHETIC DNA
FROM OLIGOS O 583, O 584, O 585 AND O 586,
TRANSFORMATION INTO E. coli Met-Ser-Lys-Thr-Cys-Tyr-Glu-Gly-Asn-Gly-His-Phe-Tyr-Arg-
Gly-Lys-Ala-Ser-Thr-Asp-Thr-Met-Gly-Arg-Pro-Cys-Leu-Pro-
Trp-Asn-Ser-Ala-Thr-Val-Leu-Gln-Gln-Thr-Tyr-His-Ala-His-
Arg-Ser-Asp-Ala-Leu-Gln-Leu-Gly-Leu-Gly-Lys-His-Asn-Tyr-
Cys-Arg-Asn-Pro-Asp-Asn-Arg-Arg-Arg-Pro-Trp-Cys-Tyr-Val-
Gln-Val-Gly-Leu-Lys-Pro-Leu-Val-Gln-Glu-Cys-Met-Val-His-
Asp-Cys-Ala-Asp-Gly-Lys-Lys-Pro-Ser-Ser-Pro-Pro-Glu-Glu-
Leu-Lys-Phe-Gln-Cys-Gly-Gln-Lys-Thr-Leu-Arg-Pro-Arg-Phe-
Lys-Ile-Ile-Gly-Gly-Glu-Phe-Thr-Thr-Ile-Glu-Asn-Gln-Pro-
Trp-Phe-Ala-Ala-Ile-Tyr-Arg-Arg-His-Arg-Gly-Gly-Ser-Val-
Thr-Tyr-Val-Cys-Gly-Gly-Ser-Leu-Ile-Ser-Pro-Cys-Trp-Val-
Ile-Ser-Ala-Thr-His-Cys-Phe-Ile-Asp-Tyr-Pro-Lys-Lys-Glu-
Asp-Tyr-Ile-Val-Tyr-Leu-Gly-Arg-Ser-Arg-Leu-Asn-Ser-Asn-
Thr-Gln-Gly-Glu-Met-Lys-Phe-Glu-Val-Glu-Asn-Leu-Ile-Leu-
His-Lys-Asp-Tyr-Ser-Ala-Asp-Thr-Leu-Ala-His-His-Asn-Asp-
Ile-Ala-Leu-Leu-Lys-Ile-Arg-Ser-Lys-Glu-Gly-Arg-Cys-Ala-
Gln-Pro-Ser-Arg-Thr-Ile-Gln-Thr-Ile-Cys-Leu-Pro-Ser-Met-
Tyr-Asn-Asp-Pro-Gln-Phe-Gly-Thr-Ser-Cys-Glu-Ile-Thr-Gly-
Phe-Gly-Lys-Glu-Asn-Ser-Thr-Asp-Tyr-Leu-Tyr-Pro-Glu-Gln-
Leu-Lys-Met-Thr-Val-Val-Lys-Leu-Ile-Ser-His-Arg-Glu-Cys-
Gln-Gln-Pro-His-Tyr-Tyr-Gly-Ser-Glu-Val-Thr-Thr-Lys-Met-
Leu-Cys-Ala-Ala-Asp-Pro-Gln-Trp-Lys-Thr-Asp-Ser-Cys-Gln-
Gly-Asp-Ser-Gly-Gly-Pro-Leu-Val-Cys-Ser-Leu-Gln-Gly-Arg-
Met-Thr-Leu-Thr-Gly-Ile-Val-Ser-Trp-Gly-Arg-Gly-Cys-Ala-
Leu-Lys-Asp-Lys-Pro-Gly-Val-Tyr-Thr-Arg-Val-Ser-His-Phe-
Ala-Leu-Ser-Pro-Val-Val-Ala-Phe-Pro-Arg-Pro-Gly-Gly-Gly-
Gly-Pro-Ser-Asp-Phe-Glu-Glu-Phe-Ser-Leu-Asp-Asp-Ile-Glu-
Gln (SEQ ID NO:44)

FIG. 18

Met-Ser-Asn-Glu-Leu-Asp-Pro-Arg-Pro-Phe-Leu-Leu-Arg-Asn-
Pro-Asn-Asp-Lys-Tyr-Glu-Pro-Phe-Trp-Glu-Asp-Glu-Glu-Lys-
Gly-Pro-His-Met-Ser-Ser-Pro-Pro-Glu-Glu-Leu-Lys-Phe-Gln-
Cys-Gly-Gln-Lys-Thr-Leu-Arg-Pro-Arg-Phe-Lys-Ile-Ile-Gly-
Gly-Glu-Phe-Thr-Thr-Ile-Glu-Asn-Gln-Pro-Trp-Phe-Ala-Ala-
Ile-Tyr-Arg-Arg-His-Arg-Gly-Gly-Ser-Val-Thr-Tyr-Val-Cys-
Gly-Gly-Ser-Leu-Ile-Ser-Pro-Cys-Trp-Val-Ile-Ser-Ala-Thr-
His-Cys-Phe-Ile-Asp-Tyr-Pro-Lys-Lys-Glu-Asp-Tyr-Ile-Val-
Tyr-Leu-Gly-Arg-Ser-Arg-Leu-Asn-Ser-Asn-Thr-Gln-Gly-Glu-
Met-Lys-Phe-Glu-Val-Glu-Asn-Leu-Ile-Leu-His-Lys-Asp-Tyr-
Ser-Ala-Asp-Thr-Leu-Ala-His-His-Asn-Asp-Ile-Ala-Leu-Leu-
Lys-Ile-Arg-Ser-Lys-Glu-Gly-Arg-Cys-Ala-Gln-Pro-Ser-Arg-
Thr-Ile-Gln-Thr-Ile-Cys-Leu-Pro-Ser-Met-Tyr-Asn-Asp-Pro-
Gln-Phe-Gly-Thr-Ser-Cys-Glu-Ile-Thr-Gly-Phe-Gly-Lys-Glu-
Asn-Ser-Thr-Asp-Tyr-Leu-Tyr-Pro-Glu-Gln-Leu-Lys-Met-Thr-
Val-Val-Lys-Leu-Ile-Ser-His-Arg-Glu-Cys-Gln-Gln-Pro-His-
Tyr-Tyr-Gly-Ser-Glu-Val-Thr-Thr-Lys-Met-Leu-Cys-Ala-Ala-
Asp-Pro-Gln-Trp-Lys-Thr-Asp-Ser-Cys-Gln-Gly-Asp-Ser-Gly-
Gly-Pro-Leu-Val-Cys-Ser-Leu-Gln-Gly-Arg-Met-Thr-Leu-Thr-
Gly-Ile-Val-Ser-Trp-Gly-Arg-Gly-Cys-Ala-Leu-Lys-Asp-Lys-
Pro-Gly-Val-Tyr-Thr-Arg-Val-Ser-His-Phe-Leu-Pro-Trp-Ile-
Arg-Ser-His-Thr-Lys-Glu-Glu-Asn-Gly-Leu-Ala-Leu
(SEQ ID NO:45)

FIG. 19

Met-Ser-Asn-Glu-Leu-Asp-Pro-Arg-Pro-Phe-Leu-Leu-Arg-Asn-
Pro-Asn-Asp-Lys-Tyr-Glu-Pro-Phe-Trp-Glu-Asp-Glu-Glu-Lys-
Gly-Pro-His-Met-Ser-Ser-Pro-Pro-Glu-Glu-Leu-Lys-Phe-Gln-
Cys-Gly-Gln-Lys-Thr-Leu-Arg-Pro-Arg-Phe-Lys-Ile-Ile-Gly-
Gly-Glu-Phe-Thr-Thr-Ile-Glu-Asn-Gln-Pro-Trp-Phe-Ala-Ala-
Ile-Tyr-Arg-Arg-His-Arg-Gly-Gly-Ser-Val-Thr-Tyr-Val-Cys-
Gly-Gly-Ser-Leu-Ile-Ser-Pro-Cys-Trp-Val-Ile-Ser-Ala-Thr-
His-Cys-Phe-Ile-Asp-Tyr-Pro-Lys-Lys-Glu-Asp-Tyr-Ile-Val-
Tyr-Leu-Gly-Arg-Ser-Arg-Leu-Asn-Ser-Asn-Thr-Gln-Gly-Glu-
Met-Lys-Phe-Glu-Val-Glu-Asn-Leu-Ile-Leu-His-Lys-Asp-Tyr-
Ser-Ala-Asp-Thr-Leu-Ala-His-His-Asn-Asp-Ile-Ala-Leu-Leu-
Lys-Ile-Arg-Ser-Lys-Glu-Gly-Arg-Cys-Ala-Gln-Pro-Ser-Arg-
Thr-Ile-Gln-Thr-Ile-Cys-Leu-Pro-Ser-Met-Tyr-Asn-Asp-Pro-
Gln-Phe-Gly-Thr-Ser-Cys-Glu-Ile-Thr-Gly-Phe-Gly-Lys-Glu-
Asn-Ser-Thr-Asp-Tyr-Leu-Tyr-Pro-Glu-Gln-Leu-Lys-Met-Thr-
Val-Val-Lys-Leu-Ile-Ser-His-Arg-Glu-Cys-Gln-Gln-Pro-His-
Tyr-Tyr-Gly-Ser-Glu-Val-Thr-Thr-Lys-Met-Leu-Cys-Ala-Ala-
Asp-Pro-Gln-Trp-Lys-Thr-Asp-Ser-Cys-Gln-Gly-Asp-Ser-Gly-
Gly-Pro-Leu-Val-Cys-Ser-Leu-Gln-Gly-Arg-Met-Thr-Leu-Thr-
Gly-Ile-Val-Ser-Trp-Gly-Arg-Gly-Cys-Ala-Leu-Lys-Asp-Lys-
Pro-Gly-Val-Tyr-Thr-Arg-Val-Ser-His-Phe-Leu-Pro-Trp-Ile-
Arg-Ser-His-Thr-Lys-Glu-Glu-Asn-Gly-Leu-Ala-Leu-Ser-Pro-
Val-Lys-Ala-Phe-Pro-Arg-Pro-Gly-Gly-Gly-Gly-Asn-Gly-Asp-
Phe-Glu-Glu-Ile-Pro-Glu-Glu-Tyr-Leu (SEQ ID NO:46)

FIG. 20

Met-Ile-Thr-Tyr-Thr-Asp-Cys-Thr-Glu-Ser-Gly-Gln-Asn-Leu-
Cys-Leu-Cys-Glu-Gly-Ser-Asn-Val-Cys-Gly-Lys-Gly-Asn-Lys-
Cys-Ile-Leu-Gly-Ser-Asp-Gly-Lys-Gly-Asn-Gln-Cys-Val-Thr-
Gly-Glu-Gly-Thr-Pro-Lys-Pro-Glu-Ser-His-Asn-Asp-Gly-Asp-
Phe-Glu-Glu-Ile-Pro-Glu-Glu-Tyr-Leu-Gln-Ile-Ser-Lys-Thr-
Cys-Tyr-Glu-Gly-Asn-Gly-His-Phe-Tyr-Arg-Gly-Lys-Ala-Ser-
Thr-Asp-Thr-Met-Gly-Arg-Pro-Cys-Leu-Pro-Trp-Asn-Ser-Ala-
Thr-Val-Leu-Gln-Gln-Thr-Tyr-His-Ala-His-Arg-Ser-Asp-Ala-
Leu-Gln-Leu-Gly-Leu-Gly-Lys-His-Asn-Tyr-Cys-Arg-Asn-Pro-
Asp-Asn-Arg-Arg-Arg-Pro-Trp-Cys-Tyr-Val-Gln-Val-Gly-Leu-
Lys-Pro-Leu-Val-Gln-Glu-Cys-Met-Val-His-Asp-Cys-Ala-Asp-
Gly-Lys-Lys-Pro-Ser-Ser-Pro-Pro-Glu-Glu-Leu-Lys-Phe-Gln-
Cys-Gly-Gln-Lys-Thr-Leu-Arg-Pro-Arg-Phe-Lys-Ile-Ile-Gly-
Gly-Glu-Phe-Thr-Thr-Ile-Glu-Asn-Gln-Pro-Trp-Phe-Ala-Ala-
Ile-Tyr-Arg-Arg-His-Arg-Gly-Gly-Ser-Val-Thr-Tyr-Val-Cys-
Gly-Gly-Ser-Leu-Ile-Ser-Pro-Cys-Trp-Val-Ile-Ser-Ala-Thr-
His-Cys-Phe-Ile-Asp-Tyr-Pro-Lys-Lys-Glu-Asp-Tyr-Ile-Val-
Tyr-Leu-Gly-Arg-Ser-Arg-Leu-Asn-Ser-Asn-Thr-Gln-Gly-Glu-
Met-Lys-Phe-Glu-Val-Glu-Asn-Leu-Ile-Leu-His-Lys-Asp-Tyr-
Ser-Ala-Asp-Thr-Leu-Ala-His-His-Asn-Asp-Ile-Ala-Leu-Leu-
Lys-Ile-arg-Ser-Lys-Glu-Gly-Arg-Cys-Ala-Gln-Pro-Ser-Arg-
Thr-Ile-Gln-Thr-Ile-Cys-Leu-Pro-Ser-Met-Tyr-Asn-Asp-Pro-
Gln-Phe-Gly-Thr-Ser-Cys-Glu-Ile-Thr-Gly-Phe-Gly-Lys-Glu-
Asn-Ser-Thr-Asp-Tyr-Leu-Tyr-Pro-Glu-Gln-Leu-Lys-Met-Thr-
Val-Val-Lys-Leu-Ile-Ser-His-Arg-Glu-Cys-Gln-Gln-Pro-His-
Tyr-Tyr-Gly-Ser-Glu-Val-Thr-Thr-Lys-Met-Leu-Cys-Ala-Ala-
Asp-Pro-Gln-Trp-Lys-Thr-Asp-Ser-Cys-Gln-Gly-Asp-Ser-Gly-
Gly-Pro-Leu-Val-Cys-Ser-Leu-Gln-Gly-Arg-Met-Thr-Leu-Thr-
Gly-Ile-Val-Ser-Trp-Gly-Arg-Gly-Cys-Ala-Leu-Lys-Asp-Lys-
Pro-Gly-Val-Tyr-Thr-Arg-Val-Ser-His-Phe-Leu-Pro-Trp-Ile-
Arg-Ser-His-Thr-Lys-Glu-Glu-Asn-Gly-Leu-Ala-Leu
(SEQ ID NO:47)

FIG. 21

PROTEINS HAVING FIBRINOLYTIC AND COAGULATION— INHIBITING PROPERTIES

BACKGROUND OF THE INVENTION

This invention relates to proteins having fibrinolytic and coagulation-inhibiting properties, which are linked at the N- and/or C-terminal end of the plasminogen-activating amino acid sequence to a thrombin- or factor Xa-inhibiting amino acid sequence, to plasmids for producing these polypeptides, and to thrombolytic agents which contain a polypeptide of this type as their active ingredient.

There are several serious diseases which are caused by the occlusion of arterial or veinous blood vessels. These thrombotic diseases include coronary thrombosis, cerebral thrombosis, pulmonary embolism, deep veinous thrombosis and peripheral arterial occlusion diseases Due to the occlusion of the blood vessels the supply of oxygen to the corresponding tissue and the exchange of nutrients and metabolites are interrupted, so that irreversible damage to the organ or tissue concerned may result.

The occlusion of a blood vessel caused by a thrombus mainly occurs at an arteriosclerotic lesion comprising fibrin, thrombocytes and erythrocytes under the action of various enzymes of the blood coagulation system. Within the enzyme cascade of the coagulation system, factor Xa and thrombin play a prominent role. Factor Xa, as a constituent of the prothrombinase complex, converts prothrombin to thrombin. Thrombin can activate all the important enzymes of the coagulation system, can induce the aggregation of thrombocytes and can lead to the formation of a fibrin network by the conversion of fibrinogen to fibrin (Furie and Furie in New Engl. J. Med. 326, 800 (1992)).

The formation of thrombuses is restricted by physiological anticoagulants, for example antithrombin III, activated protein C and tissue factor pathway inhibitor. Once formed, thrombuses can be re-dissolved by the action of plasmin occurring naturally in the body. Plasmin is formed from an inactive proenzyme, plasminogen, which is proteolytically activated by plasminogen activators. The thrombolysis due to plasmin is utilised therapeutically, by treating patients with thrombotic diseases, particularly patients with acute coronary thrombosis, with plasminogen activators. Streptokinase, APSAC (an isolated plasminogen streptokinase activator complex), double-chain urokinase (UK), recombinant single-chain urokinase (recombinant prourokinase) and tissue plasminogen activator (t-PA) are currently available for this therapy (Collen and Lijnen in Blood 78, 3114, (1991)). The following are under development: bat plasminogen activators (Gardell et al. in J. Biol. Chem. 264, 17947 (1989); EP 383 417), staphylokinase (Schlott et al. in Bio/Technology 12, 185 (1994); Collen and Van De Werf in Circulation 87 1850 (1993)), the recombinant tissue plasminogen activator BM 06.022 (Martin et al. in J. Cardiovasc. Pharm. 18, 111 (1991)) and the t-PA variant TNK-t-PA (Keyt et al. in Proc. Natl. Acad. Sci. 91, 3670 (1994)).

Streptokinase, a protein of haemolytic streptococci, activates human plasminogen, in that it forms a complex with plasminogen and thereby converts the plasminogen into an active conformation. This complex itself converts free plasminogen to plasmin, which then in turn cleaves the plasminogen bound to streptokinase. Staphylokinase, a protein obtained from *Staphylococcus aureus*, also acts similarly, but possesses a higher fibrin specificity compared with streptokinase. APSAC, a compound of streptokinase and human plasminogen which is produced in vitro, is a further development of streptokinase. Due to a chemical modification of the active center of the plasminogen, APSAC has a biological half-life which is longer than that of streptokinase.

Urokinase is a human protein which can be obtained in two forms as a proteolytically active protein from urine; high molecular weight urokinase (HUK) and low molecular weight urokinase (LUK) (Stump et al. in J. Biol. Chem. 261, 1267 (1986)). HUK and LUK are active forms of urokinase, i.e. double-chain molecules. Urokinase is formed as single-chain urokinase (prourokinase) in various tissues and can be detected in small amounts as a proenzyme in human blood (Wun et al. in J. Biol. Chem. 257, 3276 (1982)). As HUK, the activated form of prourokinase has a molecular weight of 54 kilodaltons and consists of 3 domains: the amino-terminal growth factor domain, the kringle domain and the serine protease domain (Guenzler et al. in Hoppe-Seyler's Z. Physiol. Chem. 363, 1155 (1982); Steffens et al. in Hoppe-Seyler's Z. Physiol. Chem. 363, 1043 (1982)). Although prourokinase and plasminogen are present as proenzymes, prourokinase is capable, due to its intrinsic activity, of transforming plasminogen into active plasmin. However, this plasminogen activator does not attain its full activity until the plasmin formed has itself cleaved the prourokinase between $^{158}$lysine and $^{159}$isoleucine (Lijnen et al. in J. Biol. Chem. 261, 1253 (1986)). The production of urokinase in *Escherichia coli* by genetic engineering was first described by Heyneker et al. (Proceedings of the IVth International Symposium on Genetics of Industrial Microorganisms 1982). Unglycosylated prourokinase (saruplase) is produced using a synthetic gene (Brigelius-Flohe' et al. in Appl. Microbiol. Biotech. 36, 640 (1992)).

t-PA is a protein with a molecular weight of 72 kilodaltons which is present in blood and in tissue. This plasminogen activator consists of 5 domains: the amino-terminal finger domain, the growth factor domain, kringle domain 1, kringle domain 2 and the serine protease domain. Like prourokinase, t-PA is converted into the active, double-chain form by a plasmin-catalysed cleavage between kringle domain 2 and the serine protease domain, i.e. between $^{275}$Arg and $^{276}$Ile. In vitro studies and the results of experiments on animals indicate that t-PA binds to fibrin and its enzymatic activity is stimulated by fibrin (Collen and Lijnen in Blood 78, 3114 (1991)). The fibrin specificity of t-PA should prevent the formation of plasmin in the entire blood system, resulting not only in the decomposition of fibrin decomposed but also in the decomposition of fibrinogen. A systemic plasminogen activation such as this as well as the extensive decomposition of fibrinogen are undesirable, since this increases the risk of haemorrhage. It has been shown in therapeutic practice, however, that the expectations derived from pre-clinical studies as regards the fibrin specificity of t-PA are not fulfilled. High doses, which result in systemic plasminogen activation despite this fibrin specificity, have to be infused due to the short biological half-life of t-PA (Keyt et al. in Proc. Natl. Acad. Sci. 91, 3670 (1994)).

r-PA and TNK-t-PA are variants of t-PA which possess improved properties. In r-PA (BM 06.022) the first three t-PA domains, i.e. the finger domain, the growth factor domain and the first kringle domain, have been deleted, so that the shortened molecule only contains the second kringle domain and the protease domain. r-PA is produced in *Escherichia coli* by genetic engineering and is not glycosylated. Compared with t-PA, r-PA has a longer biological half-life and more rapidly leads to reperfusion. It has been shown in experiments on animals that r-PA applied as a bolus is just as effective as a t-PA infusion (Martin et al. in J. Cardiovasc. Pharmacol. 18, 111 (1991)).

The t-PA variant TNK-t-PA differs from natural t-PA on three counts: the replacement of $^{103}$threonine by asparagine, due to which a new glycosylation site is formed; the replacement of $^{117}$asparagine by glutamine, due to which a glycosylation site is removed, and the replacement of the sequence between $^{296}$lysine and $^{299}$arginine by four successive alanine units. The combination of these three mutations results in a polypeptide with a higher fibrin specificity and a longer biological half-life compared with natural t-PA. Moreover, TNK-t-PA is considerably less inhibited by PAI-1 than is natural t-PA (Keyt et al. in Proc. Natl. Acad. Sci. 91, 3670 (1994)). Results obtained from experiments on animals in which a precursor of TNK-t-PA was used indicate that TNK-t-PA is suitable for bolus application (Refino et al. in Thromb. Haemost. 70, 313 (1993)).

Bat plasminogen activator (bat-PA) occurs in the saliva of the *Desmodus rotundus* bat. This plasminogen activator, which has meanwhile also been synthesized by genetic engineering, has an even more pronounced fibrin specificity than t-PA and in tests on animals has exhibited improved thrombolysis with an increased biological half-life and reduced systemic plasminogen activation (Gardell et al. in Circulation 84, 244 (1991)).

In the treatment of thrombotic diseases, plasminogen activators are generally administered together with an anticoagulant substance, for example heparin. This results in improved thrombolysis compared with treatment with a plasminogen activator only (Tebbe et al. in Z. Kardiol. 80, Suppl. 3, 32 (1991)). Various clinical results indicate that, in parallel with the dissolution of thrombuses, an increased tendency towards coagulation occurs (Szczeklik et al. in Arterioscl. Thromb. 12, 548 (1992) Goto et al. in Angiology 45, 273 (1994)). It is assumed that thrombin molecules which are enclosed in the thrombus and which are released again when the clot dissolves are responsible for this. Moreover, there are indications that plasminogen activators themselves also accelerate the activation of prothrombin and thus act in opposition to thrombolysis (Brommer and Meijer in Thromb. Haemostas. 70, 995 (1993)). Anticoagulant substances such as heparin, hirugen, hirudin, argatroban, protein C and recombinant tick anticoagulant peptide (TAP) can suppress this increased tendency towards re-occlusion during thrombolysis and can thus enhance the success of lysis therapy (Yao et al. in Am. J. Physiol. 262 (Heart Circ. Physiol. 31) H 347–H 379 (1992); Schneider in Thromb. Res. 64, 667 (1991); Gruber et al. in Circulation 84, 2454 (1991); Martin et al. in J. Am. Coll. Cardiol. 22, 914 (1993); Vlasuk et al. in Circulation 84, Suppl. II-467 (1991).

One of the strongest thrombin inhibitors is hirudin from the *Hirudo medicinales* leech, which consists of 65 amino acids. There are various iso-forms of hirudin, which differ as regards some of their amino acids. All iso-forms of hirudin block the binding of thrombin to a substrate, for example fibrinogen, and also block the active center of thrombin (Rydel et al. in Science 249, 277 (1990); Bode and Huber in Molecular Aspects of Inflammation, Springer, Berlin, Heidelberg, 103–115 (1991); Stone and Hofsteenge in Prot. Engineering 2, 295 (1991); Dodt et al. in Biol. Chem. Hoppe-Seyler 366, 379 (1985). In addition, smaller molecules derived from hirudin are known, which also act as thrombin inhibitors (Maraganore et al. in Biochemistry 29, 7095 (1990); Krstenansky et al. in J. Med. Chem. 30, 1688 (1987); Yue et al. in Prot. Engineering 5, 77 (1992)).

The use of hirudin in combination with a plasminogen activator for the treatment of thrombotic diseases is described in U.S. Patent No. 4,944,943 (=EP 328,957) and U.S. Pat. No. 5,126,134 (=EP 365,468). The use of hirudin derivatives in combination with a thrombolytic agent is known from International Patent Application WO 91/01142.

Hirullin is a protein containing 61 amino acids which is isolated from the *Hirudo manillensis* leech. Hirullin is identical to hirudin as regards its action and inhibitor strength, but differs very considerably from hirudin as regards its amino acid sequence. It has also proved possible to derive smaller molecules from hirullin, which are very good thrombin inhibitors (Krstenansky et al. in Febs Lett. 269, 465 (1990)).

In addition, thrombin can also be inhibited by a peptide which is derived from the amino-terminal sequence of the human thrombin receptor (Vu et al. in Nature 253, 674 (1991)). The thrombin receptor contains a thrombin-binding sequence, with an adjacent cleavage site for thrombin, in the extracellular, amino-terminal region. This sequence can inhibit thrombin provided that the cleavage site is masked by the replacement of $^{42}$serine by $^{42}$phenylalanine.

Antistasin and TAP are inhibitors of factor Xa. Antistasin is a protein from the *Haementeria ghiliani* leech, which contains 119 amino acids but has no homology of sequence with hirudin (Tuszynski et al. in J. Biol. Chem. 262, 9718 (1987); Nutt et al. in J. Biol. Chem. 263, 10162 (1988) ; Condra et al. in Thromb. Haemostas. 61, 437 (1989)). The recombinant production of antistasin has been described by Han et al. in Gene 75, 47 (1989).

TAP is a protein containing 60 amino acids from the *Onithodoros moubata* tick, which can also be produced by genetic engineering. TAP binds reversibly to factor Xa and thus acts in opposition to the formation of thrombin. The efficacy of TAP has been proved to be similar to that of hirudin or heparin in various thrombosis models (Vlasuk in Thromb. Haemost. 70, 212 (1993); Schaffer et al. in Circulation 84, 1741 (1991)).

Phaneuf et al., in Thromb. Haemost. 71, 481 (1994), describe a complex which results from a fortuitous chemical linking of streptokinase and hirudin. The plasminogen-activating capacity of this streptokinase-hirudin complex is less than that of unmodified streptokinase by a factor of 8, however.

As noted above, plasminogen-activating amino acid sequences contain various domain sites which are well known and are described in the literature.

Urokinase and prourokinase comprise the following domains:

| Domain | Amino Acids Included |
| --- | --- |
| Growth Factor Domain | amino acids 1 to 43 |
| Kringle Domain | amino acids 50 to 131 |
| Serine Protease Domain | amino acids 158 to 411 |

See Guenzler et al., "The Primary Structure of High Molecular Mass Urokinase form Human Urine; The Complete Amino Acid Sequence of the A Chain", *Hoppe-Seyler's Z. Physiol. Chem.*, 363, 1155–65 (1982); Steffens et al., "The Complete Amino Acid Sequence of Low Molecular Mass Urokinase from Human Urine", *Hoppe-Seyler's Z. Physiol. Chem.*, 363, 1043-1058 (1982).

Tissue plasminogen activator comprises the following domains:

| Domain | Amino Acids Included |
| --- | --- |
| Finger Domain | amino acids 4 to 50 |
| Growth Factor Domain | amino acids 50 to 87 |
| Kringle 1 Domain | amino acids 87 to 176 |
| Kringle 2 Domain | amino acids 176 to 262 |
| Serine Protease Domain | amino acids 276 to 527 |

See Collen et al., "Thrombolytic and Pharmacokinetic Properties of Human Tissue-Type Plasminogen Activator Variants Obtained by Deletion and/or Duplication of Structural/Functional Domains, in a Hamster Pulmonary Embolism Model", *Thrombosis and Haeomostasis,* 65, (2), 174–180 (1991).

Bat-plasminogen activator comprises the following domains:

| Domain | Amino Acids Included |
| --- | --- |
| Finger Domain | amino acids 1 to 43 |
| Growth Factor Domain | amino acids 44 to 84 |
| Kringle Domain | amino acids 92 to 173 |

Serine Protease Domain amino acids 189 to 441 See Gardell et al., "Isolation, Characterization, and cDNA Cloning of a Vampire Bat Salivary Plasminogen Activator", *Journal of Biological Chemistry,* 264, (30), 17947–952 (1989).

SUMMARY OF THE INVENTION

The underlying object of the present invention was to provide active ingredients for the treatment of vascular diseases caused by thrombosis, which effect complete thrombolysis within a very short period and which at the same time prevent vascular re-occlusion after what is initially a successful thrombolysis.

Another object of the invention was to provide a way of preventing systemic plasminogen activation by means of these active ingredients.

These and other objects of the invention have been achieved by providing a protein having fibrinolytic and coagulation-inhibiting properties, said protein comprising a plasminogen-activating amino acid sequence linked at its N- and/or C-terminal end to a thrombin- and/or factor Xa-inhibiting amino acid sequence, with the proviso that said protein is not a $^{47}$Ser to $^{411}$Leu plasminogen-activating amino acid sequence of unglycosylated prourokinase linked at its C-terminal end to a peptide sequence selected from the group consisting of $T_1$-Arg-Pro-$T_2$-Gly-Gly-Gly-Gly-Asn-Gly-Asp-Phe-Glu-Glu-Ile-Pro-Glu-Glu-Tyr-Leu-$T_3$ (SEQ ID NO:1), $T_1$-Arg-Pro-Phe-Leu-Leu-Arg-Asn-Pro-Asn-Asp-Lys-Tyr-Glu-Pro-Phe-Trp-Glu-Asp-Glu-Glu-Lys-Asn-Glu (SEQ ID NO:2), and $T_1$-Arg-Pro-Ser-Ser-Glu-Phe-Glu-Glu-Phe-Glu-Ile-Asp-Glu-Glu-Glu-Lys (SEQ ID NO:3), wherein $T_1$ is Pro or Val; $T_2$ is Leu or a direct bond between Pro and Gly, and $T_3$ is Gln or a hydroxyl group.

In accordance with another aspect of the invention the objects are achieved by providing a plasmid for producing a protein of the foregoing type having fibrinolytic properties, the plasmid comprising an operon which comprises a regulable promoter, a Shine-Dalgarno sequence effective as a ribosome binding site, a start codon, a synthetic structural gene for the protein, and 1 or 2 terminators downstream of the structural gene; the plasmid being suitable for expression of the protein in strains of *Escherichia coli*.

According to yet another aspect of the invention, the objects are also achieved by providing a method of producing a protein having fibrinolytic properties, comprising the steps of transforming an *Escherichia coli* (*E. coli*) strain with a plasmid of the foregoing type; culturing the transformed *E. coli* strain in a culture medium to express a precursor protein; lysing the *E. coli*; separating the precursor protein from the culture medium and lysed *E. coli*; solubilizing the separated precursor protein, and subsequently folding the solubilized protein by the action of a redox system to form the protein having fibrinolytic properties.

DETAILED DESCRIPTION OF PREFERRED EMBODIMENTS

It has now been found that the considerable demands imposed on such active ingredients can be fulfilled by proteins having fibrinolytic properties which contain a thrombin- and/or factor Xa-inhibiting amino acid sequence at the N- and/or C-terminal end of the plasminogen-activating amino acid sequence.

Accordingly, the present invention relates to proteins having fibrinolytic and coagulation-inhibiting properties, which are linked at the N- and/or C-terminal end of the plasminogen-activating amino acid sequence to a thrombin- and/or factor Xa-inhibiting amino acid sequence, wherein those proteins are excluded in which the $^{47}$Ser to $^{411}$Leu plasminogen-activating amino acid sequence of the unglycosylated prourokinase at the C-terminal end is linked to a peptide sequence of formula $T_1$-Arg-Pro-$T_2$-Gly-Gly-Gly-Gly-Asn-Gly-Asp-Phe-Glu-Glu-Ile-Pro-Glu-Glu-Tyr-Leu-$T_3$ (SEQ ID NO:1)

or $T_1$-Arg-Pro-Phe-Leu-Leu-Arg-Asn-Pro-Asn-Asp-Lys-Tyr-Glu-Pro-Phe-Trp-Glu-Asp-Glu-Glu-Lys-Asn-Glu (SEQ ID NO:2)

or $T_1$-Arg-Pro-Ser-Ser-Glu-Phe-Glu-Glu-Phe-Glu-Ile-Asp-Glu-Glu-Glu-Lys, (SEQ ID NO:3)

where $T_1$ is Pro or Val, $T_2$ is Leu or a direct bond between Pro and Gly, and $T_3$ is Gln or a hydroxyl group.

Preferred proteins having fibrinolytic and coagulation-inhibiting properties contain as their plasminogen-activating amino acid sequence the unaltered amino acid sequence of prourokinase (SEQ ID NO:48), at least one modified prourokinase amino acid sequence having a serine protease domain exhibiting at least 90%, and preferably at least 95%, sequence identity to the serine protease domain of the unaltered amino acid sequence of prourokinase, the unaltered amino acid sequence of urokinase, at least one modified urokinase amino acid sequence having a serine protease domain exhibiting at least 90%, and preferably at least 95%, sequence identity to the serine protease domain of the the unaltered amino acid sequence of urokinase (SEQ ID NO:49), the unaltered amino acid sequence of tissue plasminogen activator (t-PA) (SEQ ID NO:50), at least one modified t-PA amino acid sequence having a serine protease domain exhibiting at least 90%, and preferably at least 95%, sequence identity to the serine protease domain of the unaltered amino acid sequence of t-PA, the unaltered amino acid sequence of bat plasminogen activator (bat-PA), at least one modified bat-PA amino acid sequence having a serine protease domain exhibiting at least 90%, and preferably at least 95%, sequence identity to the serine protese domain of the unaltered amino acid sequence of bat-PA (SEQ ID NO:51), and/or the amino acid sequence of streptokinase (SEQ ID NO:50), staphylokinase (SEQ ID NO:55) and/or APSAC. As used herein, the term "modified" amino acid sequence refers to an amino acid sequence which has been altered by deletion, substitution, insertion and/or addition. Such deletions, substitutions, insertions and/or additions may be effected by conventional techniques which are known to persons skilled in the genetic engineering art.

In particular, the plasminogen-activating amino acid sequence in the proteins according to the invention contains the unaltered amino acid sequence of prourokinase, at least one modified prourokinase amino acid sequence having a serine protease domain exhibiting at least 90%, and preferably at least 95%, sequence identity to the serine protease domain of the unaltered amino acid sequence of prourokinase, the unaltered amino acid sequence of t-PA and/or at least one modified t-PA amino acid sequence having a serine protease domain exhibiting at least 90%, and preferably at least 95%, sequence identity to the serine protease domain of the unaltered amino acid sequence of t-PA.

In preferred embodiments of the invention, the plasminogen-activating amino acid sequence comprises a modified sequence which includes at least one kringle domain exhibiting at least 90% sequence identity to the corresponding kringle domain of the correpording unaltered sequence, and a serine protease domain exhibiting at least 90% sequence identity to the corresponding serine protease domain of the corresponding unaltered sequence.

Proteins are most preferably used in which the plasminogen-activating amino acid sequence consists of the unaltered sequence of prourokinase (SEQ ID NO:48), consisting of 411 amino acids, of the $^{47}$Ser to $^{411}$Leu amino acid sequence of prourokinase, of the $^{138}$Ser to $^{411}$Leu amino acid sequence of prourokinase, of the unaltered sequence of t-PA (SEQ ID NO:50) consisting of 527 amino acids, of the Ser-$^{89}$Arg to $^{527}$Pro amino acid sequence of t-PA, and/or of the $^{174}$Ser to $^{527}$Pro amino acid sequence of t-PA.

The thrombin- and/or factor Xa-inhibiting amino acid sequence of the proteins according to the invention preferably contains at least one amino acid sequence with properties of hirudin (SEQ ID NO:56, at least one amino acid sequence derived from human thrombin receptor (SEQ ID NO:57), at least one amino acid sequence having the properties of hirullin, antistasin (SEQ ID NO:59), and/or tick anticoagulant peptide (TAP) (SEQ ID NO:60). The thrombin- and/or factor Xa-inhibiting amino acid sequence most preferably contains at least one amino acid sequence with properties of hirudin (SEQ ID NO:55), at least one amino acid sequence derived from human thrombin receptor (SEQ ID NO:57), and/or at least one amino acid sequence with properties of hirullin (SEQ ID NO:58).

In particular, the thrombin- and/or factor Xa-inhibiting amino acid sequence contains, as the amino acid sequence with properties of hirudin, the sequence of hirudin (SEQ ID NO:56) consisting of 65 amino acids, and/or at least one amino acid sequence corresponding to the formulae

```
T₁-Arg-Pro-T₂-Gly-Gly-Gly-Gly-Asn-Gly-Asp-Phe-Glu-     (SEQ ID NO:4)

Glu-Ile-Pro-Glu-Glu-Tyr-Leu-T₃ and/or

T₄-Ile-Thr-Tyr-Thr-Asp-Cys-Thr-Glu-Ser-Gly-Gln-        (SEQ ID NO:5)

Asn-Leu-Cys-Leu-Cys-Glu-Gly-Ser-Asn-Val-Cys-Gly-

Lys-Gly-Asn-Lys-Cys-Ile-Leu-Gly-Ser-Asp-Gly-Lys-

Gly-Asn-Gln-Cys-Val-Thr-Gly-Glu-Gly-Thr-Pro-Lys-

Pro-Glu-Ser-His-Asn-Asp-Gly-Asp-Phe-Glu-Glu-Ile-

Pro-Glu-Glu-Tyr-Leu-Gln
``` and/or, as the amino acid sequence which is derived from human thrombin receptor, at least one amino acid sequence corresponding to the formulae

```
T₁-Arg-Pro-Phe-Leu-Leu-Arg-Asn-Pro-Asn-Asp-Lys-    (SEQ ID NO:6)

Tyr-Glu-Pro-Phe-Trp-Glu-Asp-Glu-Glu-Lys-Asn-Glu and/or

T₅-Ser-Asn-Glu-Leu-Asp-Pro-Arg-Pro-Phe-Leu-Leu-    (SEQ ID NO:7)

Arg-Asn-Pro-Asn-Asp-Lys-Tyr-Glu-Pro-Phe-Trp-Glu-

Asp-Glu-Glu-Lys-Gly-Pro-His-Met
``` and/or,
as the amino acid sequence with properties of hirullin, at least one amino acid sequence corresponding to the formulae

```
T₁-Arg-Pro-Ser-Ser-Glu-Phe-Glu-Glu-Phe-Glu-Ile-    (SEQ ID NO:8)

Asp-Glu-Glu-Lys and/or

T₁-Arg-Pro-T2-Gly-Gly-Gly-Gly-Pro-Ser-Asp-Phe-Glu-    (SEQ ID NO:9)

Glu-Phe-Ser-Leu-Asp-Asp-Ile-Glu-Gln.
```

In these amino acid sequences, $T_1$ represents Pro or Val, $T_2$ represents a direct bond between Pro and Gly, $T_3$ represents a hydroxyl group or a direct bond to the adjacent amino acid, $T_4$ represents Met, Ile or a direct bond to the adjacent amino acid, and $T_4$ represents Met, Ile or a direct bond to the adjacent amino acid.

Via its N- and/or C-terminal end, the plasminogen-activating amino acid sequence is linked to a thrombin- and/or factor Xa-inhibiting amino acid sequence directly, or via the amino acid isoleucine, or via a peptide sequence of general formulae Ser-$X_1$-$X_2$-$X_3$-$X_4$-$X_5$-$X_6$-$X_7$ (SEQ ID NO:10)
or
Ile-Ser-$X_1$-$X_2$-$X_3$-$X_4$-$X_5$-$X_6$-$X_7$ (SEQ ID NO:11).

The variables in the bridging sequence have the following meanings: $X_1$ is Pro or Leu; $X_2$ is Gly, Val or Pro; $X_3$ is Lys, Val, Arg, Gly or Glu; $X_4$ is Ala, Val, Gly, Leu or Ile; $X_5$ is Gly, Phe, Trp, Tyr or Val; $X_6$ is Gly, Pro or a direct bond to the adjacent amino acid, and $X_7$ is Ile or a direct bond to the adjacent amino acid.

Compared with known plasminogen activators, compared with known mixtures comprising a plasminogen activator and a thrombin inhibitor, and compared with the known streptokinase-hirudin complex, the proteins according to the invention are distinguished by a stronger fibrinolytic effect combined with surprisingly good thrombin-inhibiting properties. In addition, plasma fibrinogen is consumed in considerably smaller amounts by the polypeptides according to the invention. The effect of the significantly higher fibrin specificity which results from this, particularly by comparison even with the known mixtures comprising a plasminogen activator and a thrombin inhibitor, is that the coagulation capacity of the blood is only slightly affected and the risk of uncontrolled haemorrhages as possible complications of systemic fibrinogen decomposition is minimized. The high fibrin specificity of the proteins according to the invention thus permits bolus applications with a significantly reduced risk of haemorrhage compared with bolus applications of known thrombolytic agents.

Accordingly, the present invention also relates to thrombolytic agents which contain a protein according to the invention as their active ingredient.

0.1 to 1 mg of a polypeptide according to the invention is required per kg for the treatment of vascular occlusions caused by thrombosis, for example coronary thrombosis, cerebral thrombosis, peripheral acute arterial occlusion, pulmonary embolism and deep veinous thrombosis of the legs and pelvis. The proteins according to the invention can be administered parenterally by bolus injection or infusion. Proteins according to the invention, the coagulation-inhibiting properties of which are exclusively due to thrombin-inhibiting amino acid sequences or to thrombin- and factor Xa-inhibiting amino acid sequences, are particularly suitable for the treatment of acute conditions, for the treatment of coronary thrombosis for example. Proteins according to the invention, the coagulation-inhibiting properties of which are exclusively due to factor Xa-inhibiting amino acid sequences, are particularly suitable for the treatment of chronic thrombotic diseases, for example deep vein thrombosis or unstable angina pectoris.

In addition to at least one polypeptide according to the invention, the thrombolytic agents according to the invention may contain auxiliary materials or adjuvants, for example carriers, solvents, diluents, colorants and binders. The choice of these auxiliary materials, as well as the amounts thereof to be used, depends on how the drug is to be administered, and is considered within the skill of the art.

The proteins according to the invention are produced using genetic engineering methods. For this purpose the corresponding genes from synthetic oligonucleotides are cloned into suitable plasmids and expressed in *Escherichia coli* with control of the trp- or tac promoter, particularly with control of the trp promoter.

Accordingly, the present invention also relates to plasmids for use in the production of proteins according to the invention, the operons of which comprise a regulable promoter, a Shine-Dalgarno sequence which is effective as a ribosome binding site, a start codon, a synthetic structural gene for a protein according to the invention, and one or two terminators downstream of the structural gene.

The plasmids according to the invention are expressed in *Escherichia coli* strains, particularly in *Escherichia coli* strains of group K 12, for example *E. coli* K 12 JM 101 (ATCC 33876), *E. coli* K 12 JM 103 (ATCC 39403), *E. coli* K 12 JM 105 (DSM 4162) and *E. coli* K 12 DH 1 (ATCC 33849). In the bacterial cell, the polypeptides according to the invention occur in high yield in inclusion bodies in which the protein is present in denatured form. After isolating the inclusion bodies, the denatured protein is folded into the desired tertiary structure, by a protein chemistry technique, under the action of a redox system.

BRIEF DESCRIPTION OF THE DRAWINGS

The invention will be described in further detail hereinafter with reference to representative examples illustrated in the accompanying drawings in which:

FIG. 18 shows the amino acid sequence of peptide M36 (SEQ ID NO:44);

FIG. 19 shows the amino acid sequence of peptide M51 (SEQ ID NO:45);

FIG. 20 shows the amino acid sequence of peptide M5112 (SEQ ID NO:46); and

FIG. 21 shows the amino acid sequence of peptide sequence M43 (SEQ ID NO:47).

EXAMPLES

Figure 1:
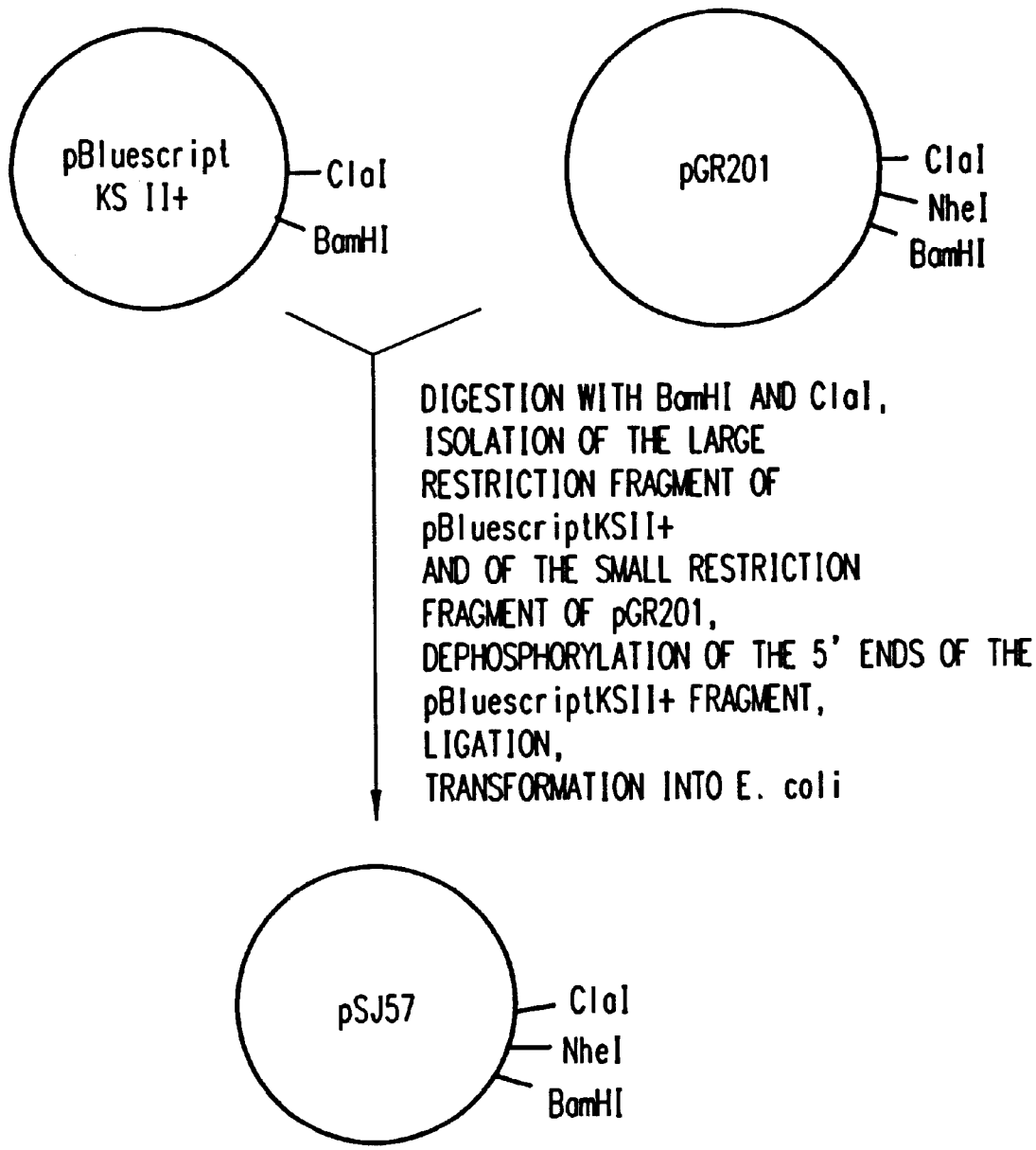
FIGS. 1 through 17 are schematic illustrations of the steps for preparing expression plasmids for producing the proteins of the present invention.
Figure 2:
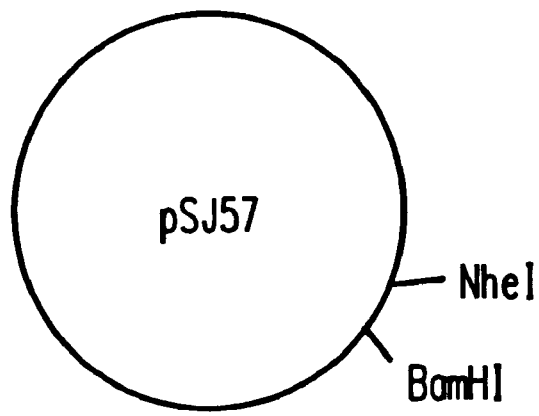
Figure 2:
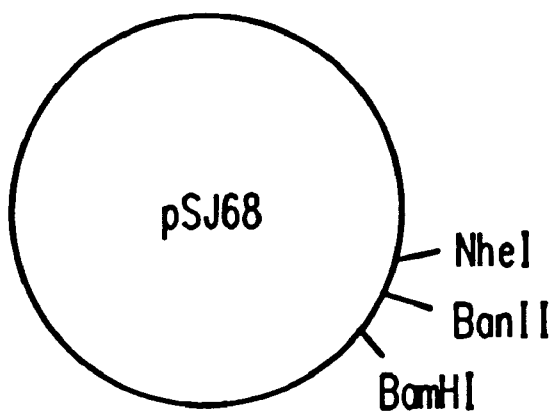
Figure 3:
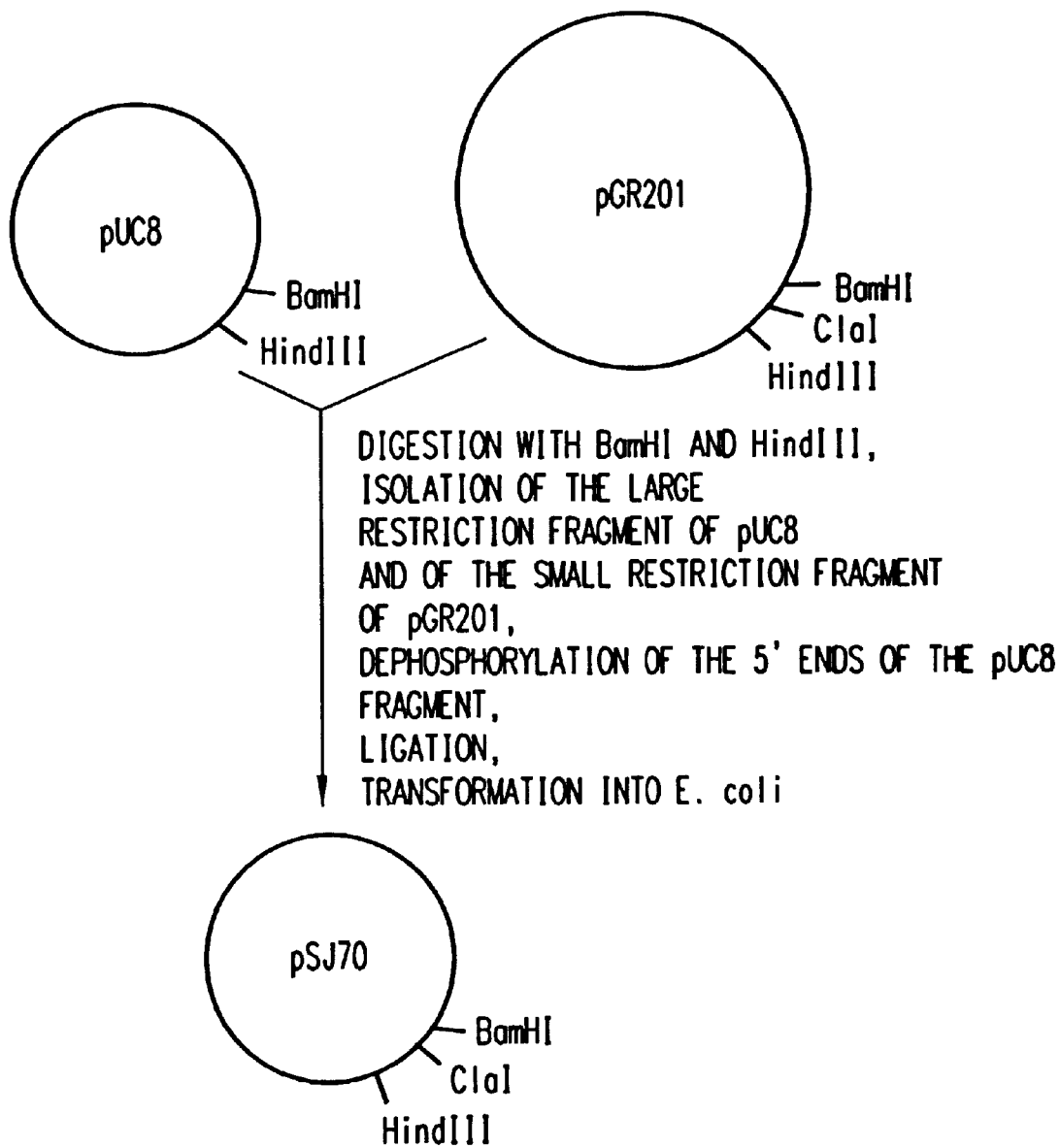
Figure 4:
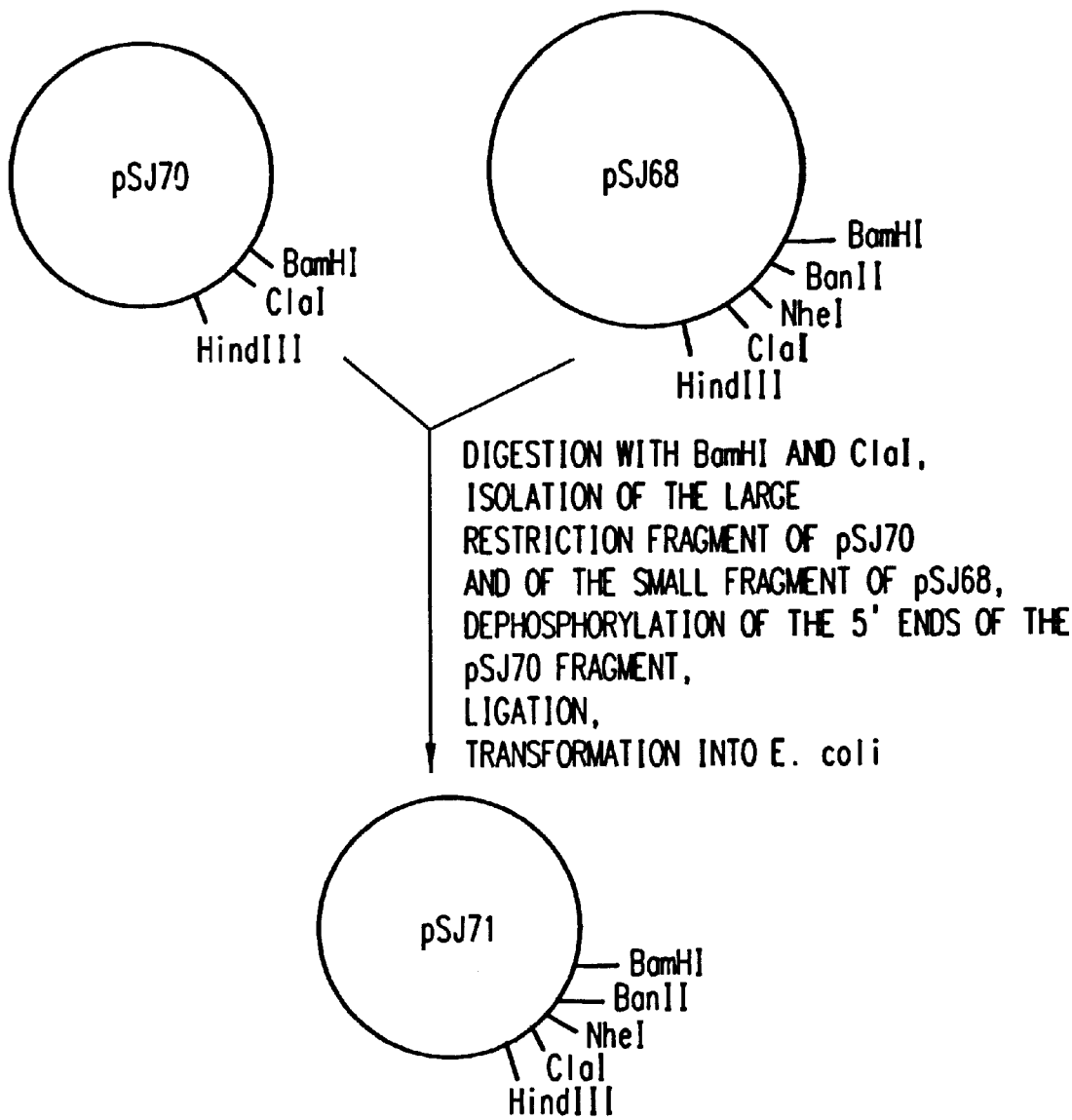
Figure 5:
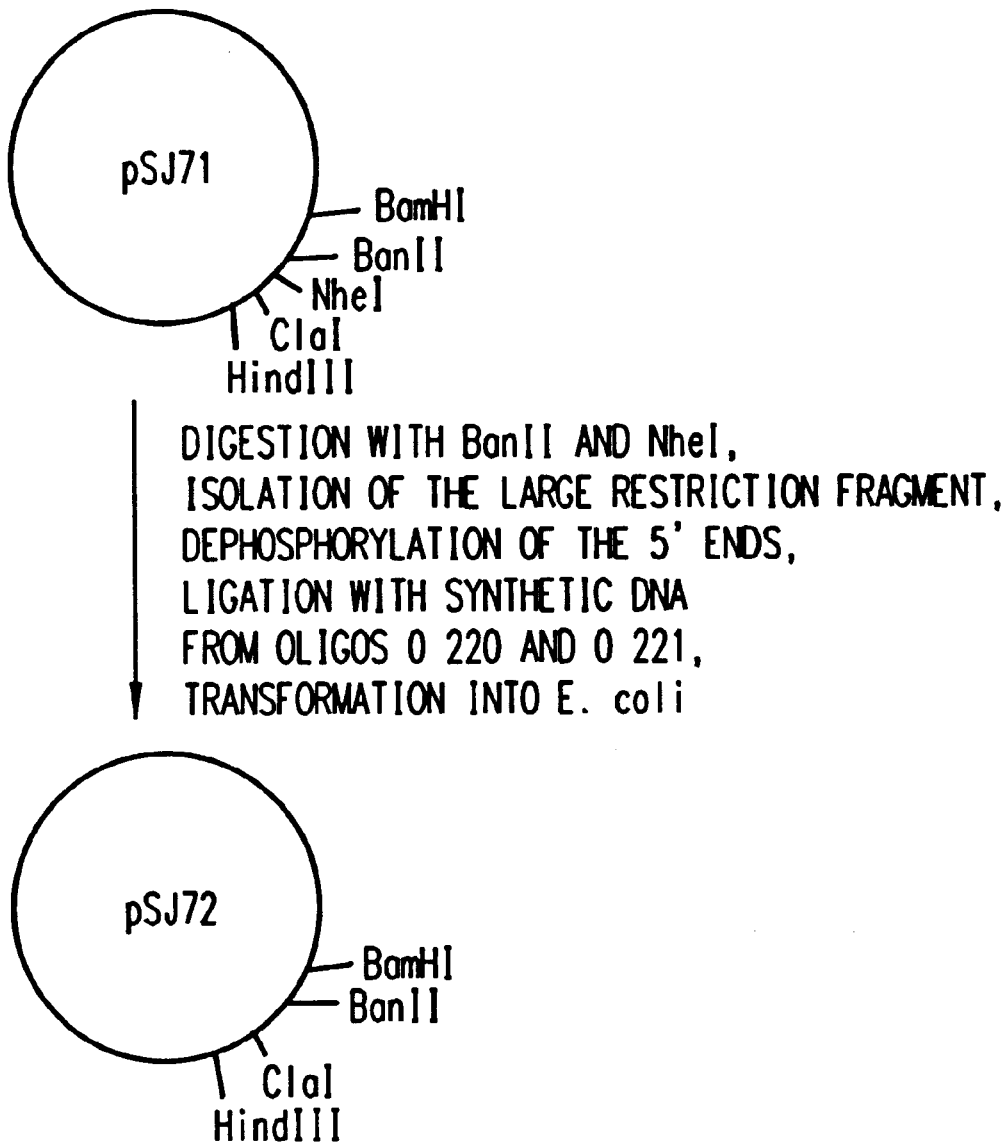
Figure 6:
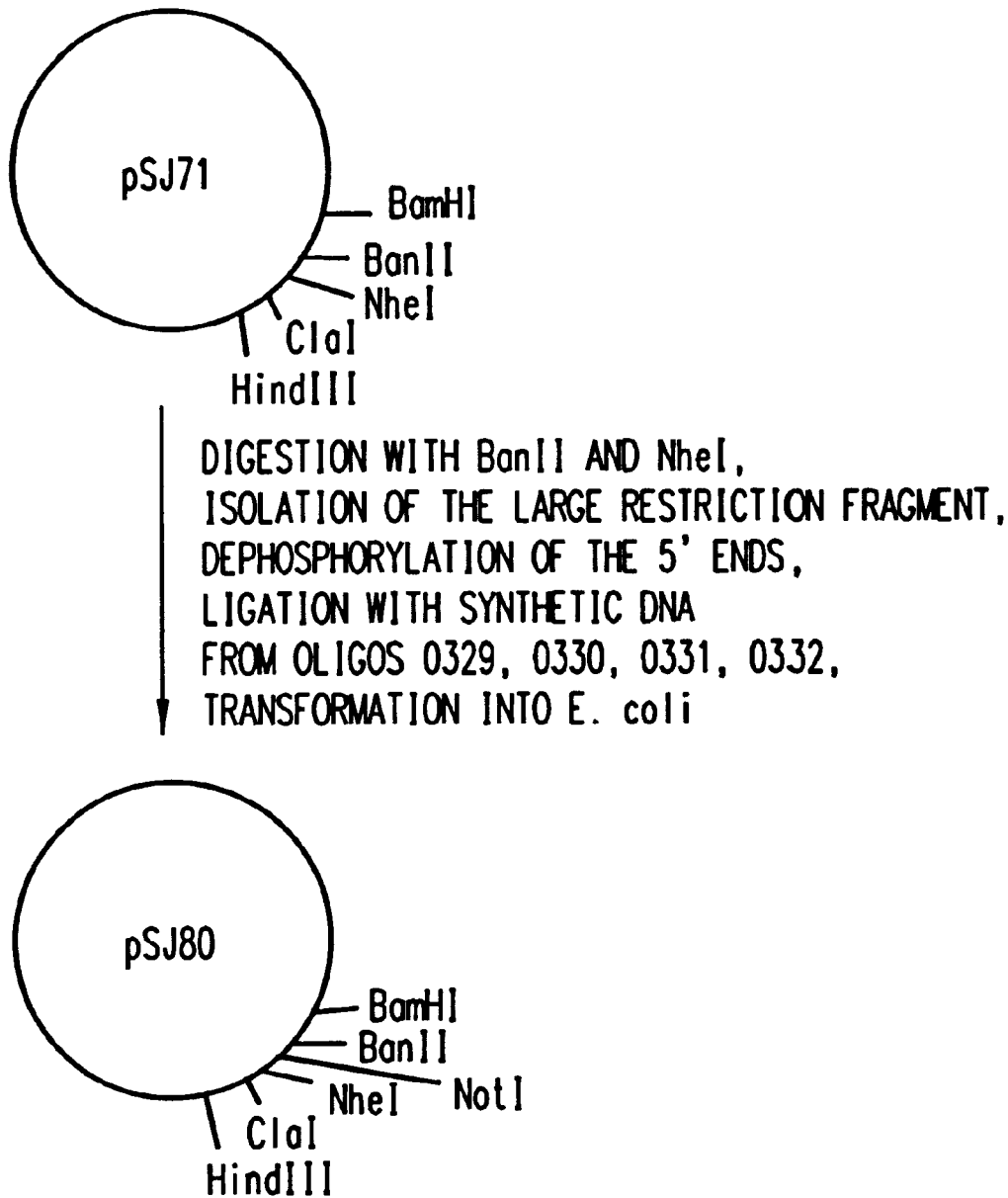
Figure 7:
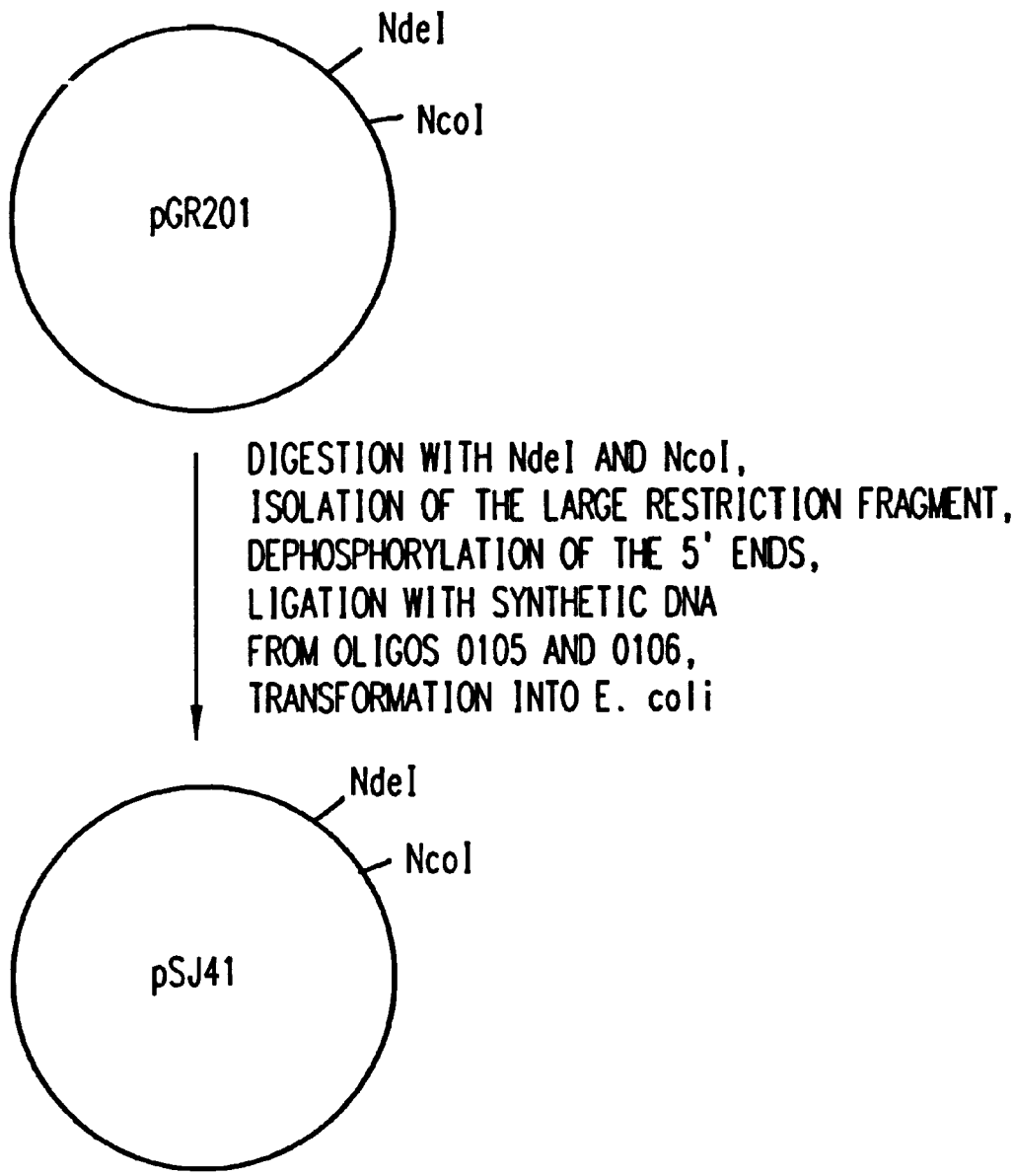
Figure 8:
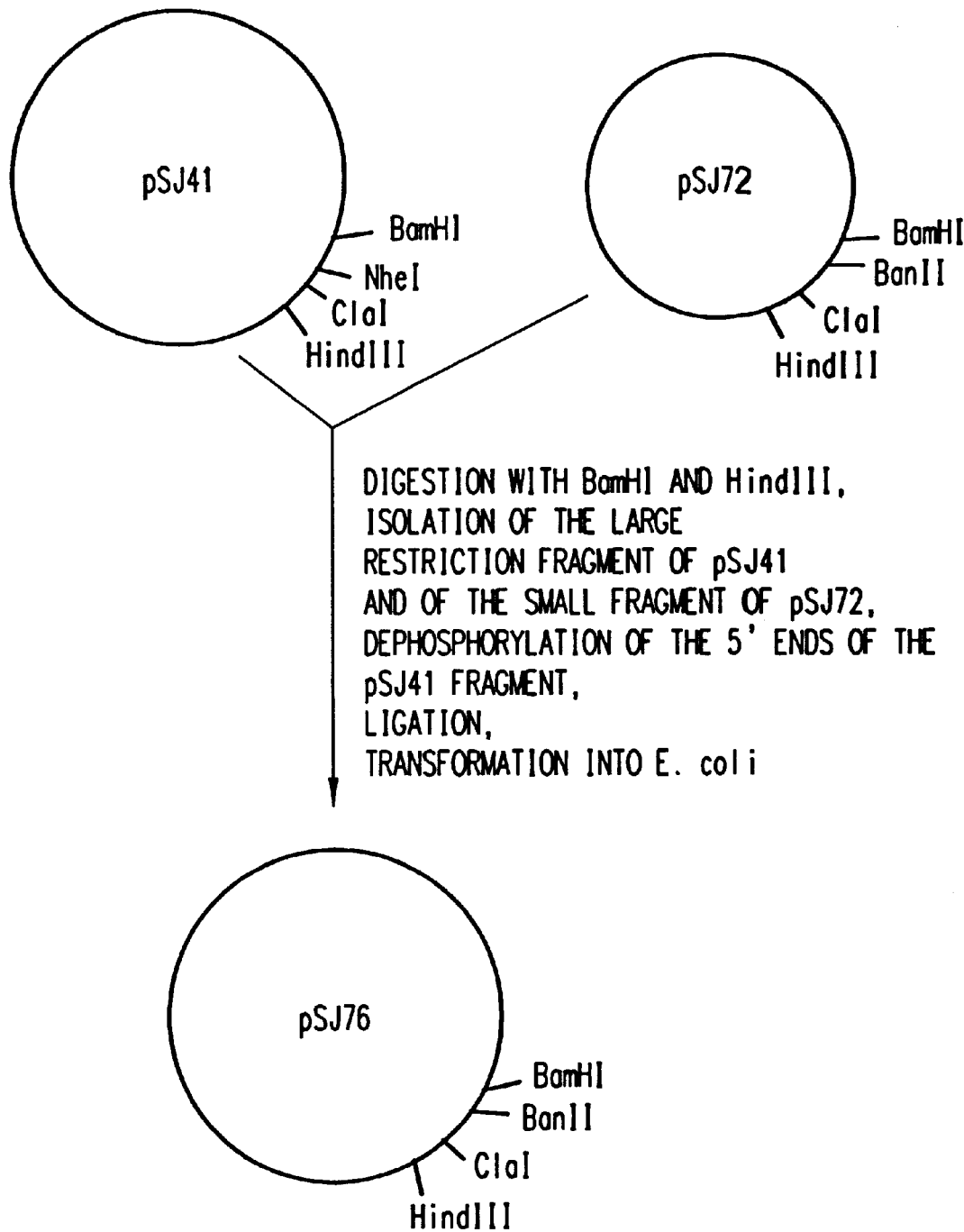
Figure 9:
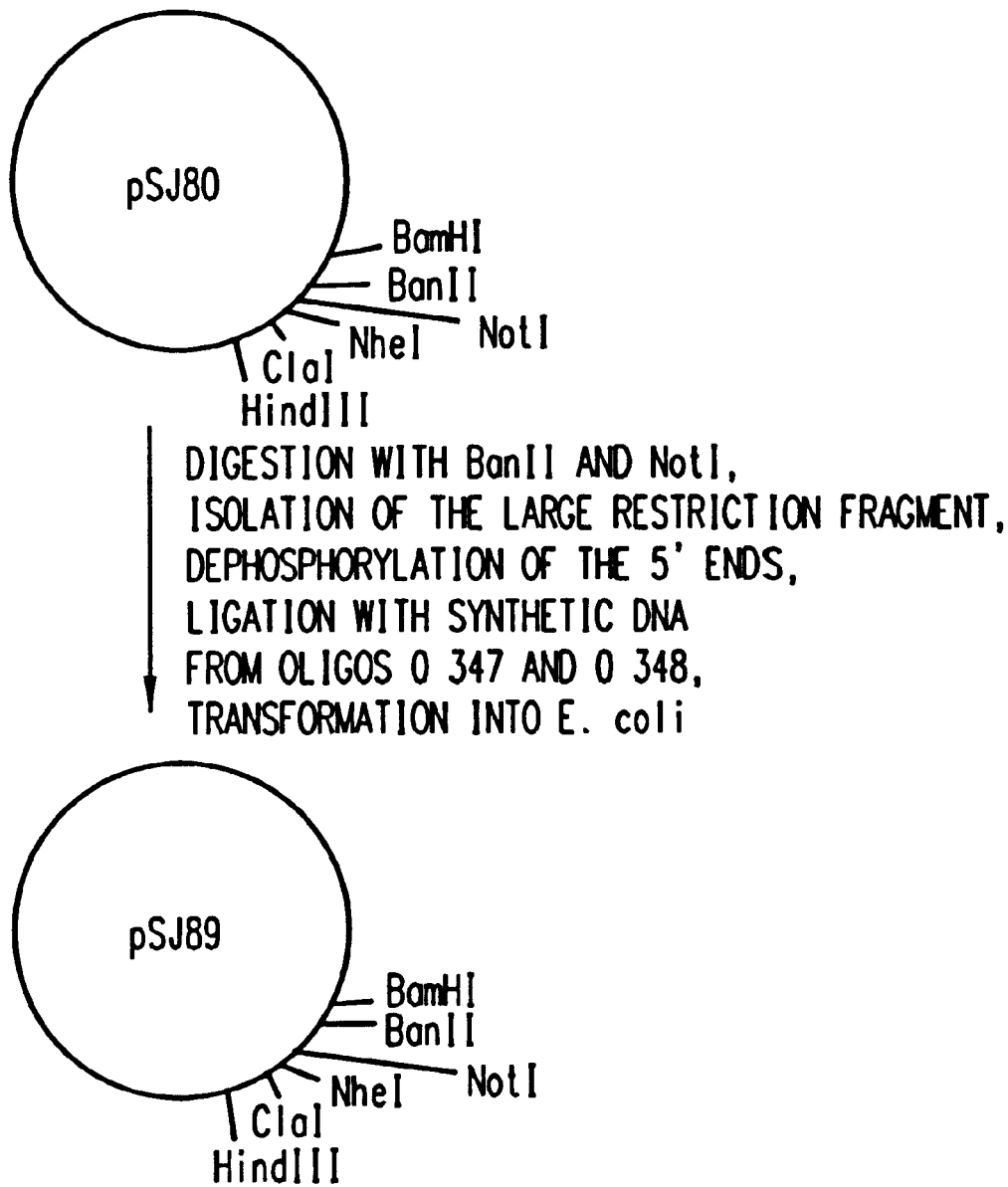
Figure 10:
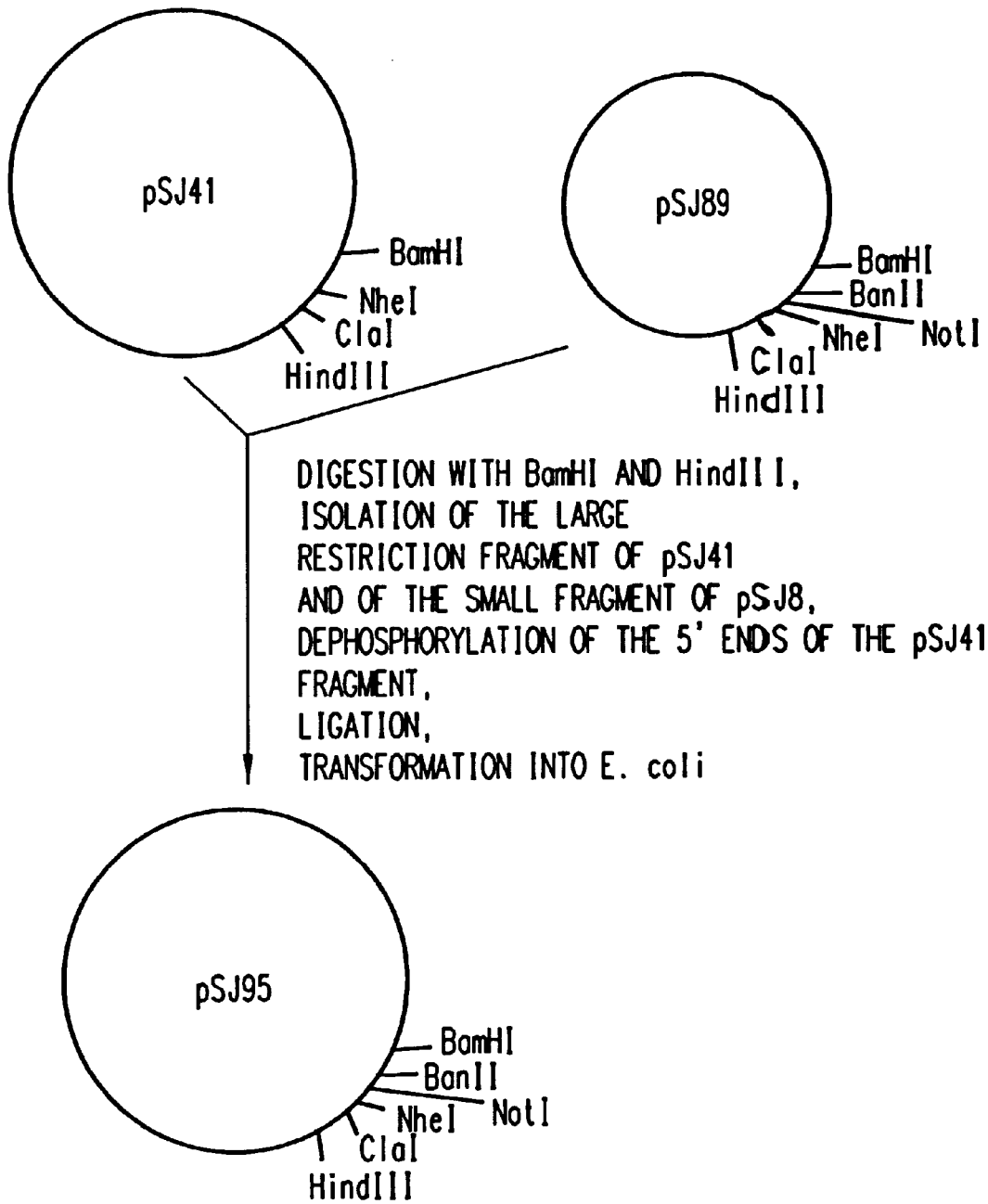
Figure 11:
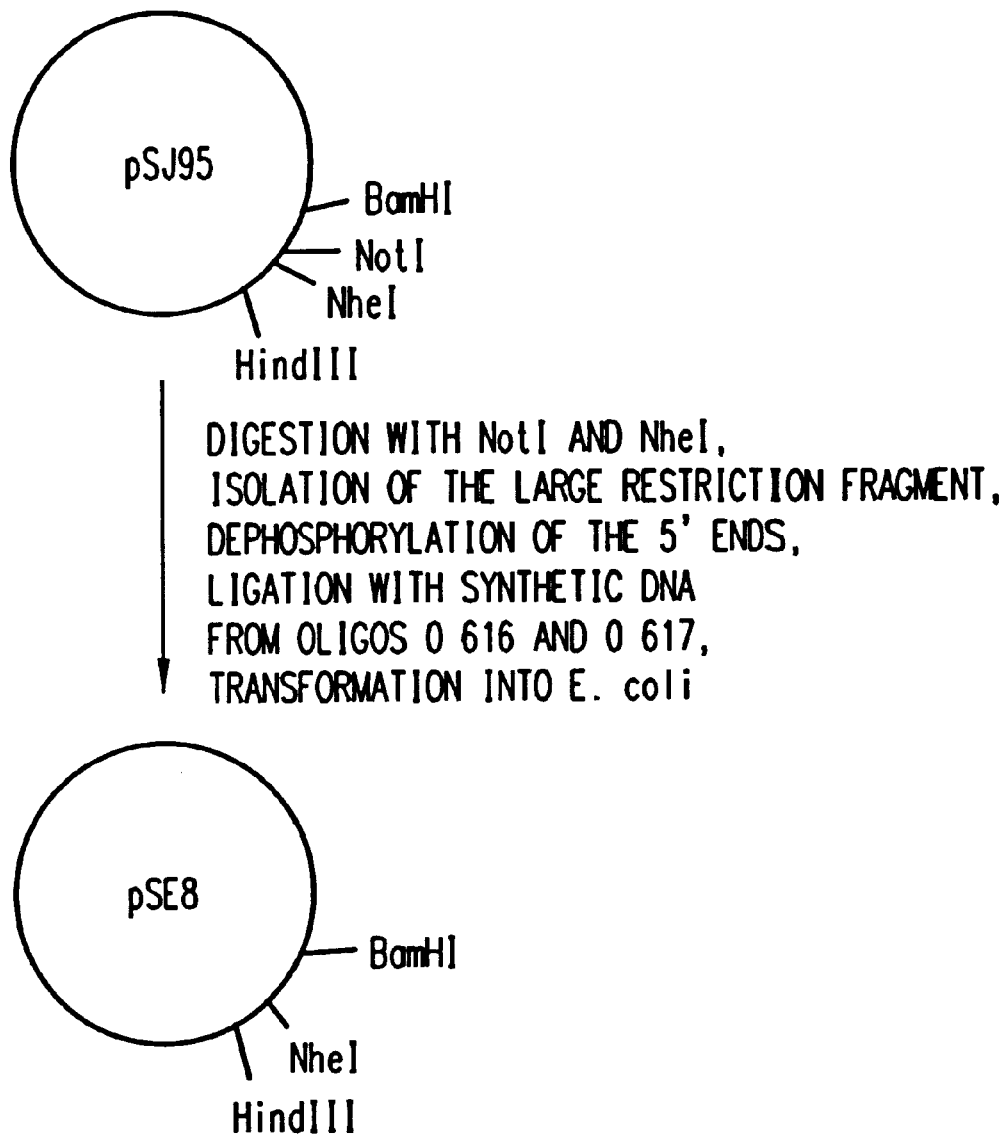
Figure 12:
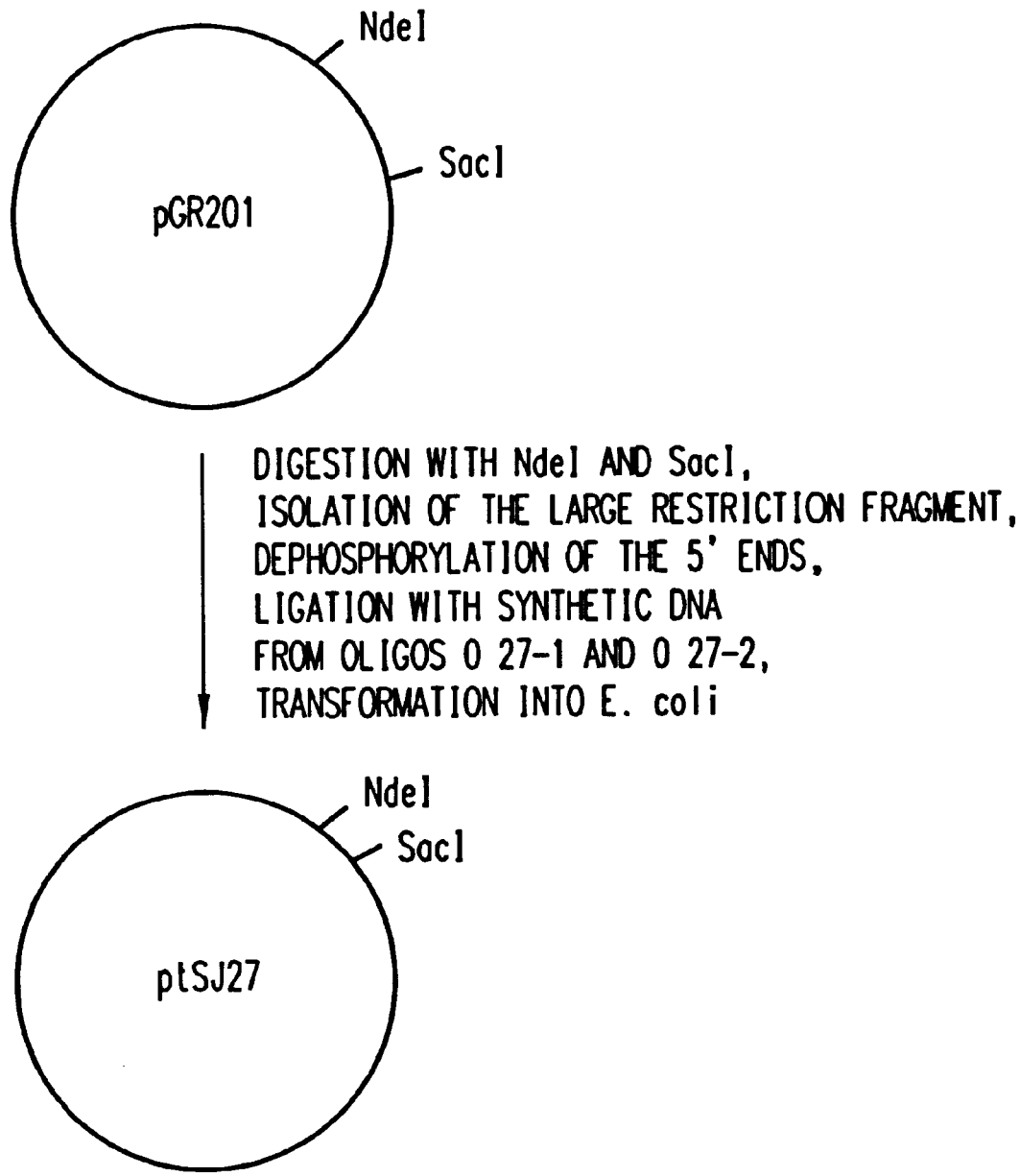
Figure 13:
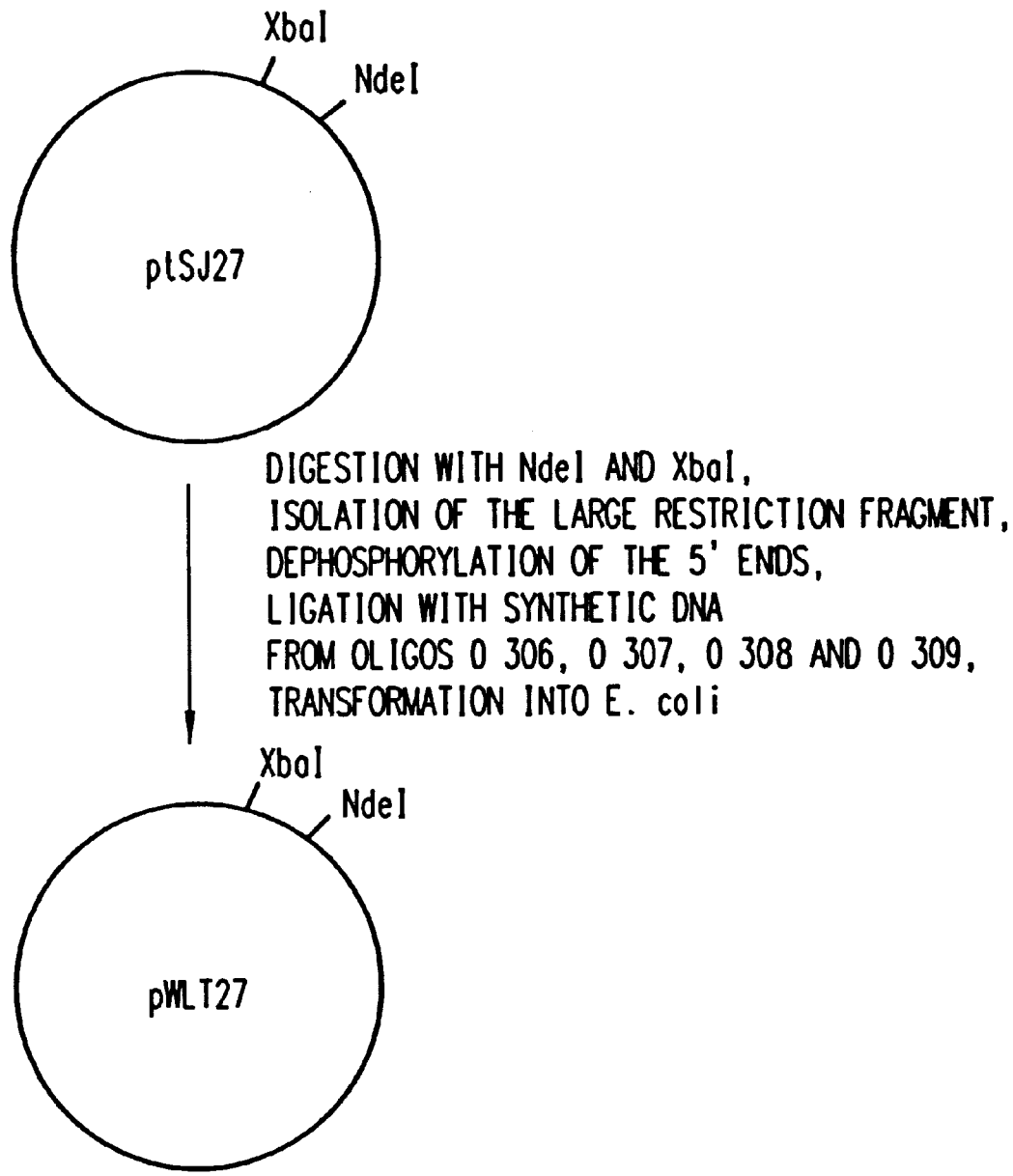
Figure 14:
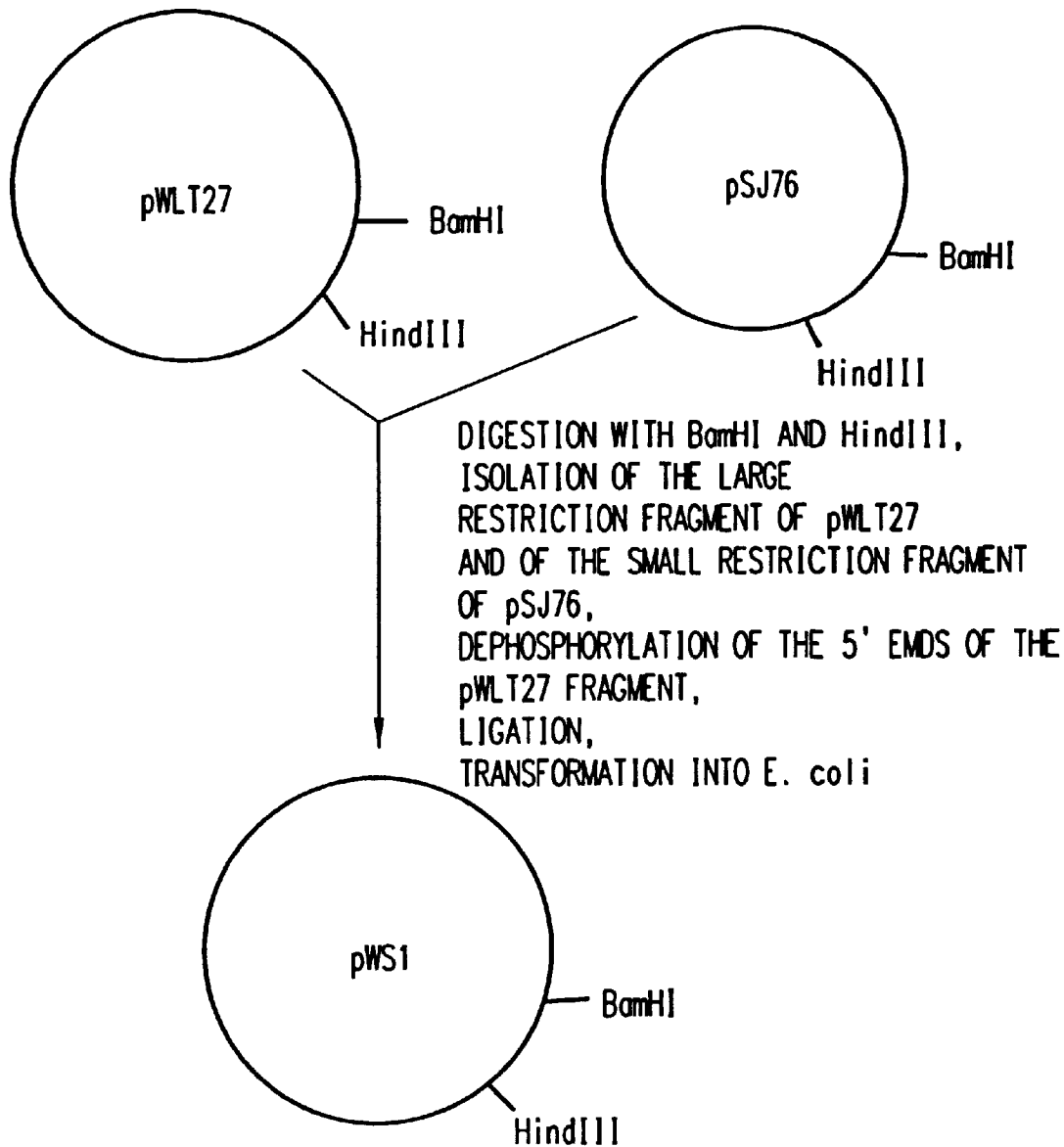
Figure 15:
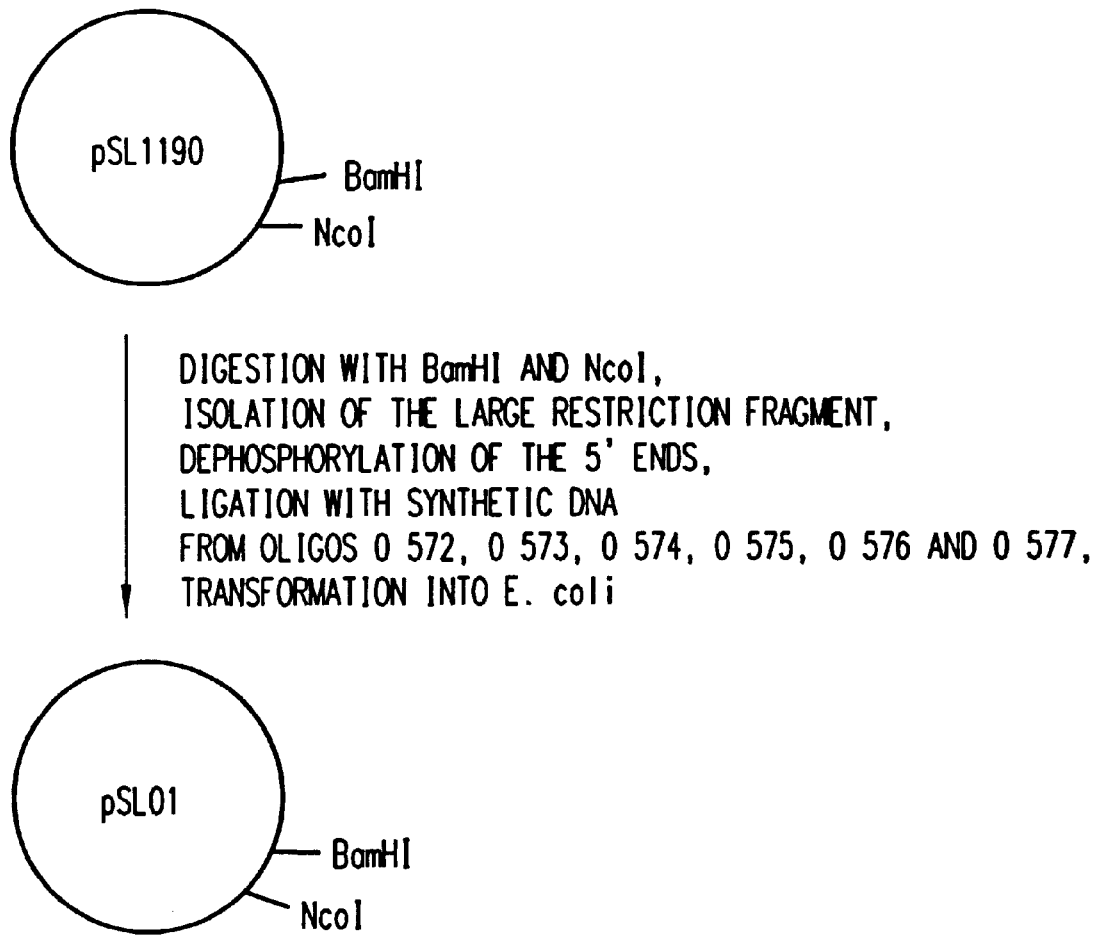
Figure 16:
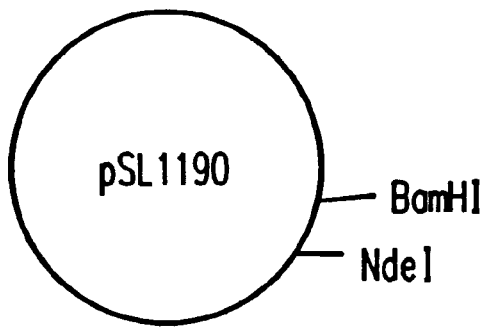
Figure 16:
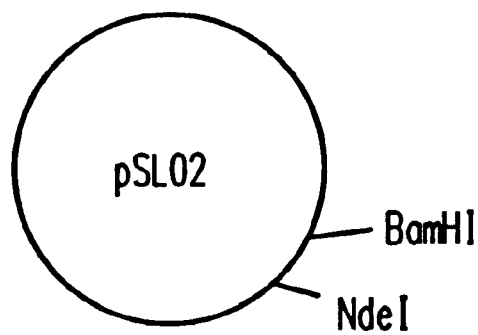
Figure 17:
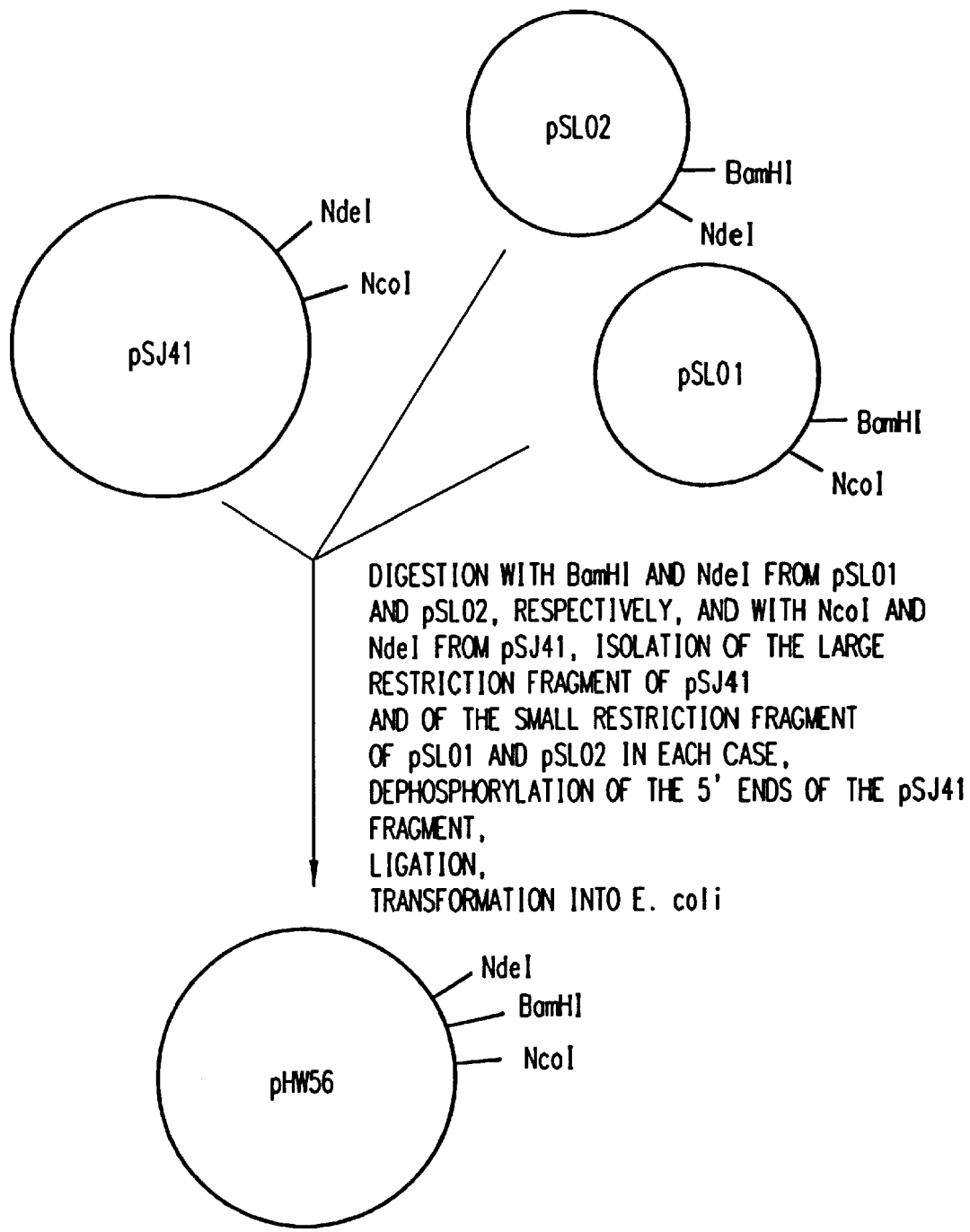

1. Preparation, isolation and purification of proteins according to the invention
a) Cloning operations The expression plasmids for the production by genetic engineering of the polypeptides according to the invention in *Escherichia coli* were prepared using techniques known in the art. The sequence of the individual preparation steps is illustrated in FIGS. 1 to 17. The starting materials for the preparation of the plasmids were the plasmids pBluescript KS II+ (manufactured by Stratagene, Heidelberg), pUC8 (manufactured by Pharmacia, Freiburg), and pGR201. pGR201 is identical to plasmid pBF160 described in EP 408 945 and Appl. Microbiol. Biotechn. 36, 640–649 (1992). The restriction endonucleases BanII, BamHI, ClaI, HindIII, NcoI, NdeI, NheI, NotI, SacI and XbaI, and the DNA-modifying enzymes such as the alkaline phosphatase, T4 ligase, T4 kinase and T7 polymerase, were obtained from the companies Pharmacia, Stratagene, Boehringer Mannheim and Gibco (Eggenstein). The changes in the plasmids during their preparation were verified by restriction analysis and DNA sequencing. DNA sequencing was effected according to the manufacturer's instructions, using a collection of reagents supplied by Pharmacia. Various oligodeoxyribonucleotides (oligos) were used in the preparation of the plasmids; their sequences, together with the associated designations, are given in Table 1.

The oligodeoxyribonucleotides were prepared in detritylated form on an 0.1 μmolar scale, by means of a synthesiser (Model 391) supplied by Applied Biosystems (Weiterstadt) according to the manufacturer's data, using β-cyanoethyl-protected diisopropylamino-phosphoamidites. 100 pmoles of each oligodeoxyribonucleotide were phosphorylated with one T4 kinase enzyme unit in the presence of 10 mM adenosine triphosphate in 50 mM tri(hydroxymethyl aminomethane/HCl (tris-HCl), 10 mM magnesium chloride and 5 mM dithiothreitol at a pH of 7.5 and subsequently transformed to double-strand DNA molecules in the same buffer. The synthetic double-strand DNA molecules obtained were purified by gel electrophoresis on a polyacrylamide gel (5% polyacrylamide) and subsequently used in the ligation with the correspondingly prepared plasmids. Preparation of the plasmids by digestion with restriction enzymes, isolation of the corresponding restriction fragments and dephosphorylation of the 5'-ends, subsequent ligation and transformation into *E. coli* K12 JM103, as well as all other genetic engineering operations, were effected in the manner known in the art, and are given by Sambrook et al. in "Molecular Cloning: A Laboratory Manual", Second Edition, Cold Spring Harbor Laboratory Press, Cold Spring Harbour, USA, 1989.

TABLE 1

| Oligo | Sequence written from 5' to 3' | |
|---|---|---|
| O 105 | TATGAGCAAAACTTGCTACGAAGGTAACGGTCACTTCTACCGTGGTA AGGCTTCTACCGACAC | (SEQ ID NO:12) |
| O 106 | CATGGTGTCGGTAGAAGCCTTACCACGGTAGAAGTGACCGTTACCTT CGTAGCAAGTTTTGCTCA | (SEQ ID NO:13) |
| O 220 | CGGTTAAGGCTTTCCCGAGGCCTGGTGGTGGTGGTAACGGTGACTTC GAAGAAATCCCGGAAGAGTACCTGTGATAGGATCAA | (SEQ ID NO:14) |
| O 221 | CTAGTTGATCCTATCACAGGTACTCTTCCGGGATTTCTTCGAAGTCA CCGTTACCACCACCACCAGGCCTCGGGAAAGCCTTAACGGGCT | (SEQ ID NO:15) |
| O 265 | CACCCGGCGGAGACGGCGGGCTCAGAGCCAGACCGTTTTCTTCTTTG GTGTGAGAACG | (SEQ ID NO:16) |
| O 27-1 | TATGAGTAGTCCACCAGAAGAGCT | (SEQ ID NO:17) |
| O 27-2 | GAGCTCTTCTGGTGGACTACTCA | (SEQ ID NO:18) |
| O 281 | CGTCCGGGTGGTGGTGGTAACGGTGACTTCGAAGAAATCCCGGAAGA ATACCTGTAAG | (SEQ ID NO:19) |
| O 282 | GATCCGTTCTCACACCAAAGAAGAAAACGGTCTGGCTCTGAGCCCGC CGTCTCCGCCGGGTGGTTTCCCG | (SEQ ID NO:20) |
| O 283 | CTAGCTTACAGGTATTCTTCCGGGATTTCTTCGAAGTCACCGTTACC ACCACCACCCGGACGCGGGAAAC | (SEQ ID NO:21) |
| O 306 | ACGTAACCCGAATGACAAATACGAACCGTTCTGGGAAGATGAAGAGA | (SEQ ID NO:22) |

TABLE 1-continued

| Oligo | Sequence written from 5' to 3' | |
|---|---|---|
| | AAGGGCCCCA | |
| O 307 | CTAGATAAGGAGGAAATAATATGAGCAATGAACTTGACCCGCGTCCG | (SEQ ID NO:23) |
| | TTCCTGCT | |
| O 308 | CATTCGGGTTACGTAGCAGGAACGGACGCGGGTCAAGTTCATTGCTC | (SEQ ID NO:24) |
| | ATATTATTTCCTCCTTAT | |
| O 309 | TATGGGGCCCTTTCTCTTCATCTTCCCAGAACGGTTCGTATTTGT | (SEQ ID NO:25) |
| O 329 | AAGAAATCCCGGAAGAATACCTGCAATAAG | (SEQ ID NO:26) |
| O 330 | CGGTTAAGGCTTGGGGACCGCGGCCGCTGGGTGGTGGTGGTAACGGT | (SEQ ID NO:27) |
| | GACTTCG | |
| O 331 | ACCACCACCCAGCGGCCGCGGTCCCCAAGCCTTAACCGGGCT | (SEQ ID NO:28) |
| O 332 | CTAGCTTATTGCAGGTATTCTTCCGGGATTTCTTCGAAGTCACCGTT | (SEQ ID NO:29) |
| | ACC | |
| O 347 | CGGTTGTTGCTTTCCCGC | (SEQ ID NO:30) |
| O 348 | GGCCGCGGGAAAGCAACAACCGGGCT | (SEQ ID NO:31) |
| O 572 | CATGGTGTCGGTAGAAGCCTTACCACGGTAGAAGTGGCCGTTACCTT | (SEQ ID NO:32) |
| | CGTAGCAAGTTTTA | |
| O 573 | GAGATCTGCAGGTATTCTTCCGGGATTTCTTCGAAGTCACCGTCGTT | (SEQ ID NO:33) |
| | GTGAGATTCC | |
| O 574 | GGTTTCGGAGTACCTTCACCAGTAACGACCTGGTTACCTTTACCGTC | (SEQ ID NO:34) |
| | G | |
| O 575 | GATCCGACGGTAAAGGTAACCAGTGCGTTACTGGTGAAGGTACTCCG | (SEQ ID NO:35) |
| | AAACCGGAATCTCACAACGACG | |
| O 576 | GCCACTTCTACCGTGGTAAGGCTTCTACCGACAC | (SEQ ID NO:36) |
| O 577 | GTGACTTCGAAGAAATCCCGGAAGAATACCTGCAGATCTCTAAAACT | (SEQ ID NO:37) |
| | TGCTACGAAGGTAACG | |
| O 583 | GCAAACGTTAGAACCTTCGCACAGGCACAGGTTCTGACCAGATTCAG | (SEQ ID NO:38) |
| | TGCAGTCAGTGTACGTAATCA | |
| O 584 | GATCCCAGGATGCATTTGTTACCTTTACC | (SEQ ID NO:39) |
| O 585 | GAAGGTTCTAACGTTTGCGGTAAAGGTAACAAATGCATCCTGG | (SEQ ID NO:40) |
| O 586 | TATGATTACGTACACTGACTGCACTGAATCTGGTCAGAACCTGTGCC | (SEQ ID NO:41) |
| | TGTGC | |
| O 616 | CTAGCTTATTGTTCAATGTCGTCCAGAGAGAATTCTTCGAAGTCGCT | (SEQ ID NO:42) |
| | CGGACCACCACCACCC | |
| O 617 | GGCCGGGTGGTGGTGGTCCGAGCGACTTCGAAGAATTCTCTCTGGAC | (SEQ ID NO:43) |
| | GACATTGAACAATAAG | | b) Preparation of reusable cultures and fermentation

The recombinant expression plasmids pHW56 (M 43), pWLT27 (M 51), pWS1 (M 5112) and pSE8 (M 36) were introduced into *E. coli* K12 JM103 (ATCC 39403) and plated on standard I-nutrient agar (Merck, 150 mg/l ampicillin) (Sambrook et al. "Molecular Cloning: A Laboratory Manual"). A single colony of each transformation was cultivated in standard I-nutrient broth (Merck, pH 7.0; 150 mg/l ampicillin) at 20° C. to an optical density (OD) of 1 at 578 nm, and, with the addition of dimethyl sulfoxide (DMSO) (final concentration 7.5%), was frozen at and stored at −70° C. in 2 ml portions as a reusable culture. To produce the polypeptides according to the invention, 1 ml of each reusable culture was suspended in 20 ml standard I-nutrient broth (pH 7.0; 150 mg/l ampicillin) and cultivated at 37° C. to an OD of 1 at 578 nm.

The entire amount of culture obtained was then suspended in 1 liter of standard I-nutrient broth (pH 7.0; 150 mg/l ampicillin) and fermented in shaken flasks at 37° C. Induction was effected by adding 2 ml of indole-acrylacetic acid solution (60 mg in 2 ml ethanol) at an OD of 0.5 to 1 at 578 nm.

c) Expression testing

In order to test the expression rate, cells corresponding to 1 ml of a cell suspension with an OD of 1 at 578 nm were centrifuged directly before induction and every hour after induction (total 6 hours). The sedimented cells were digested with lysozyme (1 mg lysozyme per ml in 50 mM tris-HCl buffer, pH 8.0, 50 mM ethylenediaminetetra-acetic acid (EDTA) and 15% saccharose). The homogenate from the lysed cells was solubilized in 4–5 M guanidinium hydrochloride solution and after diluting to 1.2 M guanidinium hydrochloride and adding a reducing agent (glutathione or cysteine) was subjected to the folding reaction for 2–5 hours (Winkler et al., Biochemistry 25, 4041 to 4045 (1986)). The single-chain polypeptides according to the invention which were obtained were transformed into the corresponding double-chain molecules by the addition of plasmin, and the activity of the double-chain molecules was determined with the chromogen substrate pyro-Glu-Gly-Arg-p-nitroanilide. Activation of the polypeptides according to the invention with plasmin was effected in 50 mM tris-HCl buffer, 12 mM sodium chloride, 0.02% tween 80 at pH 7.4 and 37° C. The ratio of polypeptide according to the invention to plasmin was about 8000–36,000 to 1, based on enzyme units. The test incubation was effected in 50 mM tris-HCl buffer and 38 mM sodium chloride at pH 8.8 in the presence of 0.36 $\mu$M aprotinine (to inhibit the plasmin) and 0,27 mM of pyro-Glu-Gly-Arg-p-nitroanilide substrate at 37° C. Depending on the concentration of the polypeptide according to the invention, the reaction was stopped after an incubation period of 5 to 60 minutes by adding 50% acetic acid, and the extinction at 405 nm was measured. According to the information from the manufacturer of the substrate (Kabi Vitrum, Sweden), in this procedure a change in extinction of 0.05 per minute at 405 nm corresponds to a urokinase activity of 25 ploug units per ml of test solution. The polypeptides according to the invention had specific activities between 120,000 and 155,000 ploug units per mg of protein. The protein content of the solutions was determined using the BCA assay of the Pierce company.

d) Isolation and purification

After 6 hours, the fermentation carried out under the conditions described in 1b) was terminated (density 5–6 OD at 578 nm) and the cells were extracted by centrifuging. The cell sediment was re-suspended in 20D ml water and digested in a high-pressure homogeniser. After renewed centrifuging, the sediment, which contained the entire amount of single-chain polypeptide according to the invention, was dissolved in 500 ml S M guanidinium hydrochloride, 40 mM cysteine, 1 mM EDTA at a pH of 8.0 and diluted with 2000 ml 25 mM tris-HCl with a pH of 9.0. The folding reaction was complete after about 12 hours.

After adding 8 g silica gel, the polypeptides according to the invention which were obtained were completely bound to silica gel by stirring for 2 hours. The loaded silica gel was separated and washed with acetate buffer (pH 4) The polypeptides were eluted with 0.5 M trimethylammonium chloride (TMAC) in 0.1 M acetate buffer (pH 4.0). After two chromatographic separations (copper chelate column and cation exchanger) the polypeptides were obtained in pure form. Their single-chain character was established by N-terminal sequence analysis.

All the isolated polypeptides according to the invention, the amino acid sequences of which are given in FIGS. 18 to 21, exhibited no activity or only very slight activity (less than 1%) in a direct activity test with the chromogen substrate for urokinase. Full enzyme activity was only obtained after cleavage with plasmin (the conditions are given in Section 1c). The polypeptides according to the invention were accordingly expressed as single-chain proteins in *E.coli* K12 JM103.

2. Determination of the thrombin-inhibiting effect

The inhibitor effect of the polypeptides according to the invention was determined by measuring the thrombin time, by mixing 200 $\mu$l of a 1:10 dilution of human citrate plasma in veronal buffer with 50 $\mu$l of thrombin solution (0.2 units) and 50 $\mu$l of an aqueous solution containing 0.5–50 $\mu$g of a polypeptide according to the invention. The time to the formation of a fibrin network was then measured. The measured inhibition factors, which illustrate the prolongation of the thrombin time in the presence of a polypeptide according to the invention, are listed in Table 2.

TABLE 2

Prolongation of the thrombin time by polypeptides according to the invention

| Polypeptide according to the invention | Inhibition Factor[1] |
|---|---|
| M51 | 1.2 |
| M5112 | 3.0 |
| M36 | 2.8 |
| M43 | 1.2 |

[1]with respect to the effect of 5 $\mu$g protein Inhibition factor = the ratio of the thrombin time in the presence of an inhibitor to the thrombin time in the absence of an inhibitor.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A plasmid selected from the group consisting of pWLT27, pWS1, pSE8 and pHW56 for producing a protein having fibrinolytic and coagulation-inhibiting properties.

2. A method of constructing a plasmid selected from the group consisting of pWLT27, pWS1, pSE8 and pHW56, wherein said plasmid pWLT27 is constructed from plasmid pGR201, said plasmid pWSE1 is constructed from plasmids pBluescript KS II+, pUC8 and pGR201, said plasmid pSE8 is constructed from plasmids pBluescript KS II+, pUC8 and pGR201, and said plasmid pHW56 is constructed from plasmids pSL1190 and pGR201.

3. An isolated protein having fibrinolytic and coagulation-inhibiting properties produced by a host cell transformed with a plasmid of claim 1.

4. A method of producing a protein having fibrinolytic properties, said method comprising the steps of:

transforming an *Escherichia coli* (*E. coli*) strain with a plasmid according to claim 1;

culturing the transformed *E. coli* strain in a culture medium to express a precursor protein;

lysing the *E. coli*;

separating the precursor protein from the culture medium and lysed *E. coli*;

solubilizing the separated precursor protein; and subsequently folding the solubilized protein by the action of a redox system to form the protein having fibrinolytic properties.

5. A thrombolytic composition comprising an effective thrombolytic amount of a protein according to claim 3, and at least one pharmaceutically acceptable carrier or adjuvant.

6. A thrombolytic composition according to claim 5, wherein the composition is adapted for oral administration.

7. A host cell transformed with a plasmid according to claim 1.

8. A host cell according to claim 7, wherein the host cell is an *Escherichia coli* cell.

* * * * *

SEQUENCE LISTING (1) GENERAL INFORMATION:

(iii) NUMBER OF SEQUENCES: 60

(2) INFORMATION FOR SEQ ID NO: 1:

-continued

```
    (i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (v) FRAGMENT TYPE: C-terminal (ix) FEATURE:
        (A) NAME/KEY: Modified-site
        (B) LOCATION:<1..21
        (D) OTHER INFORMATION:/product= "Xaa"
            /label= Xaa
            /note= "Pos 1: Xaa = Pro, Val
            Pos 4: Xaa = Leu, Peptide bond
            Pos 21: Xaa = Gln, Hydroxyl function"

(xi) SEQUENCE DESCRIPTION: SEQ ID NO: 1:

Xaa Arg Pro Xaa Gly Gly Gly Gly Asn Gly Asp Phe Glu Glu Ile Pro
1               5                   10                  15

Glu Glu Tyr Leu Xaa
            20

(2) INFORMATION FOR SEQ ID NO: 2:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (v) FRAGMENT TYPE: C-terminal (ix) FEATURE:
        (A) NAME/KEY: Modified-site
        (B) LOCATION:1..2
        (D) OTHER INFORMATION:/product= "Xaa"
            /label= Xaa
            /note= "Pos 1: Xaa = Pro, Val"

(xi) SEQUENCE DESCRIPTION: SEQ ID NO: 2:

Xaa Arg Pro Phe Leu Leu Arg Asn Pro Asn Asp Lys Tyr Glu Pro Phe
1               5                   10                  15

Trp Glu Asp Glu Glu Lys Asn Glu
            20

(2) INFORMATION FOR SEQ ID NO: 3:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (v) FRAGMENT TYPE: C-terminal (ix) FEATURE:
        (A) NAME/KEY: Modified-site
        (B) LOCATION:1..2
        (D) OTHER INFORMATION:/product= "Xaa"
            /label= Xaa
            /note= "Pos 1: Xaa = Pro, Val"

(xi) SEQUENCE DESCRIPTION: SEQ ID NO: 3:

Xaa Arg Pro Ser Ser Glu Phe Glu Glu Phe Glu Ile Asp Glu Glu Glu
1               5                   10                  15
```

Lys (2) INFORMATION FOR SEQ ID NO: 4:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (v) FRAGMENT TYPE: C-terminal (ix) FEATURE:
        (A) NAME/KEY: Modified-site
        (B) LOCATION:1..21
        (D) OTHER INFORMATION:/product= "Xaa"
            /label= Xaa
            /note= "Pos 1: Xaa = Pro, Val
            Pos 4: Xaa = Leu, Peptide bond
            Pos 21: Xaa = Gln, Hydroxyl function,
            Peptide bond"

(xi) SEQUENCE DESCRIPTION: SEQ ID NO: 4:

Xaa Arg Pro Xaa Gly Gly Gly Gly Asn Gly Asp Phe Glu Glu Ile Pro
1             5                  10               15

Glu Glu Tyr Leu Xaa
         20

(2) INFORMATION FOR SEQ ID NO: 5:

(i) SEQUENCE CHARACTERISTICS:
        (A) LENGTH: 66 amino acids
        (B) TYPE: amino acid
        (C) STRANDEDNESS:
        (D) TOPOLOGY: linear (ii) MOLECULE TYPE: peptide (v) FRAGMENT TYPE: C-terminal (ix) FEATURE:
        (A) NAME/KEY: Modified-site
        (B) LOCATION:1..21
        (D) OTHER INFORMATION:/product= "Xaa"
           /label= Xaa
           /note= "Pos 1: Xaa = Met, Ile, Peptide bond"

(xi) SEQUENCE DESCRIPTION: SEQ ID NO: 5:

Xaa Ile Thr Tyr Thr Asp Cys Thr Glu Ser Gly Gln Asn Leu Cys Leu
1             5                  10               15

Cys Glu Gly Ser Asn Val Cys Gly Lys Gly Asn Lys Cys Ile Leu Gly
         20                 25               30

Ser Asp Gly Lys Gly Asn Gln Cys Val Thr Gly Glu Gly Thr Pro Lys
         35                 40               45

Pro Glu Ser His Asn Asp Gly Asp Phe Glu Glu Ile Pro Glu Glu Tyr
         50                 55               60

Leu Gln
65

(2) INFORMATION FOR SEQ ID NO: 6:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide

```
        (v) FRAGMENT TYPE: C-terminal (ix) FEATURE:
            (A) NAME/KEY: Modified-site
            (B) LOCATION:1..2
            (D) OTHER INFORMATION:/product= "Xaa"
                 /label= Xaa
                 /note= "Pos 1: Xaa = Pro, Val"

(xi) SEQUENCE DESCRIPTION: SEQ ID NO: 6:

Xaa Arg Pro Phe Leu Leu Arg Asn Pro Asn Asp Lys Tyr Glu Pro Phe
    1               5                  10                  15

Trp Glu Asp Glu Glu Lys Asn Glu
                20

(2) INFORMATION FOR SEQ ID NO: 7:

(i) SEQUENCE CHARACTERISTICS:
            (A) LENGTH: 32 amino acids
            (B) TYPE: amino acid
            (C) STRANDEDNESS:
            (D) TOPOLOGY: linear (ii) MOLECULE TYPE: peptide (v) FRAGMENT TYPE: C-terminal (ix) FEATURE:
            (A) NAME/KEY: Modified-site
            (B) LOCATION:1..2
            (D) OTHER INFORMATION:/product= "Xaa"
                 /label= Xaa
                 /note= "Pos 1: Xaa = Met, Peptide bond"

(xi) SEQUENCE DESCRIPTION: SEQ ID NO: 7:

Xaa Ser Asn Glu Leu Asp Pro Arg Pro Phe Leu Leu Arg Asn Pro Asn
    1               5                  10                  15

Asp Lys Tyr Glu Pro Phe Trp Glu Asp Glu Glu Lys Gly Pro His Met
                20                  25                  30

(2) INFORMATION FOR SEQ ID NO: 8:

(i) SEQUENCE CHARACTERISTICS:
            (A) LENGTH: 17 amino acids
            (B) TYPE: amino acid
            (C) STRANDEDNESS:
            (D) TOPOLOGY: linear (ii) MOLECULE TYPE: peptide (v) FRAGMENT TYPE: C-terminal (ix) FEATURE:
            (A) NAME/KEY: Modified-site
            (B) LOCATION:1..2
            (D) OTHER INFORMATION:/product= "Xaa"
                 /label= Xaa
                 /note= "Pos 1: Xaa = Pro, Val"

(xi) SEQUENCE DESCRIPTION: SEQ ID NO: 8:

Xaa Arg Pro Ser Ser Glu Phe Glu Glu Phe Glu Ile Asp Glu Glu Glu
    1               5                  10                  15

Lys (2) INFORMATION FOR SEQ ID NO: 9:

(i) SEQUENCE CHARACTERISTICS:
            (A) LENGTH: 22 amino acids
            (B) TYPE: amino acid
            (C) STRANDEDNESS:
```

```
          (D) TOPOLOGY: linear (ii) MOLECULE TYPE: peptide (v) FRAGMENT TYPE: C-terminal (ix) FEATURE:
          (A) NAME/KEY: Modified-site
          (B) LOCATION:1..5
          (D) OTHER INFORMATION:/product= "Xaa"
              /label= Xaa
              /note= "Pos 1: Xaa = Pro, Val
              Pos 4: Xaa = Leu, Peptide bond"

(xi) SEQUENCE DESCRIPTION: SEQ ID NO: 9:

Xaa Arg Pro Xaa Gly Gly Gly Gly Pro Ser Asp Phe Glu Glu Phe Ser
 1               5                  10                  15

Leu Asp Asp Ile Glu Gln
                20

(2) INFORMATION FOR SEQ ID NO: 10:

(i) SEQUENCE CHARACTERISTICS:
          (A) LENGTH: 8 amino acids
          (B) TYPE: amino acid
          (C) STRANDEDNESS:
          (D) TOPOLOGY: linear (ii) MOLECULE TYPE: peptide (v) FRAGMENT TYPE: C-terminal (ix) FEATURE:
          (A) NAME/KEY: Modified-site
          (B) LOCATION:2..5
          (D) OTHER INFORMATION:/product= "Xaa"
              /label= Xaa
              /note= "Pos 2: Xaa = Pro, Leu
              Pos 3: Xaa = Gly, Val, Pro;
              Pos 4: Xaa = Lys, Val, Arg, Gly, Glu
              Pos 5: Xaa = Ala, Val, Gly, Leu, Ile"

(ix) FEATURE:
          (A) NAME/KEY: Modified-site
          (B) LOCATION:6..8
          (D) OTHER INFORMATION:/product= "Xaa"
              /label= Xaa
              /note= "Pos 6: Xaa = Gly, Phe, Trp, Tyr, Val
              Pos 7: Xaa = Gly, Pro, Peptide bond
              Pos 8: Xaa = Ile, Peptide bond"

(xi) SEQUENCE DESCRIPTION: SEQ ID NO: 10:

Ser Xaa Xaa Xaa Xaa Xaa Xaa Xaa
 1               5

(2) INFORMATION FOR SEQ ID NO: 11:

(i) SEQUENCE CHARACTERISTICS:
          (A) LENGTH: 9 amino acids
          (B) TYPE: amino acid
          (C) STRANDEDNESS:
          (D) TOPOLOGY: linear (ii) MOLECULE TYPE: peptide (v) FRAGMENT TYPE: C-terminal (ix) FEATURE:
          (A) NAME/KEY: Modified-site
          (B) LOCATION:3..6
          (D) OTHER INFORMATION:/product= "Xaa"
              /label= Xaa
              /note= "Pos 3: Xaa = Pro, Leu
              Pos 4: Xaa = Gly, Val, Pro
              Pos 5: Xaa = Lys, Val, Arg, Gly, Glu
```

```
            Pos 6: Xaa = Ala, Val, Gly, Leu, Ile"

(ix) FEATURE:
         (A) NAME/KEY: Modified-site
         (B) LOCATION:7..9
         (D) OTHER INFORMATION:/product= "Xaa"
             /label= Xaa
             /note= "Pos 7: Xaa = Gly, Phe, Trp, Tyr, Val
             Pos 8: Xaa = Gly Pro, Peptide bond
             Pos 9: Xaa = Ile, Peptide bond"

(xi) SEQUENCE DESCRIPTION: SEQ ID NO: 11:

Ile Ser Xaa Xaa Xaa Xaa Xaa Xaa Xaa
    1               5

(2) INFORMATION FOR SEQ ID NO: 12:

(i) SEQUENCE CHARACTERISTICS:
         (A) LENGTH: 63 base pairs
         (B) TYPE: nucleic acid
         (C) STRANDEDNESS: single
         (D) TOPOLOGY: linear (ii) MOLECULE TYPE: other nucleic acid
         (A) DESCRIPTION:  /desc = " Synthetic DNA;
             Nucleotide sequence for Oligo O105"

(iii) HYPOTHETICAL: NO (iv) ANTI-SENSE: NO (xi) SEQUENCE DESCRIPTION: SEQ ID NO: 12:

TATGAGCAAA ACTTGCTACG AAGGTAACGG TCACTTCTAC CGTGGTAAGG CTTCTACCGA      60

CAC                                                                   63

(2) INFORMATION FOR SEQ ID NO: 13:

(i) SEQUENCE CHARACTERISTICS:
         (A) LENGTH: 65 base pairs
         (B) TYPE: nucleic acid
         (C) STRANDEDNESS: single
         (D) TOPOLOGY: linear (ii) MOLECULE TYPE: other nucleic acid
         (A) DESCRIPTION:  /desc = "Synthetic DNA;
             Nucleotide sequence for Oligo O106"

(iii) HYPOTHETICAL: NO (iv) ANTI-SENSE: NO (xi) SEQUENCE DESCRIPTION: SEQ ID NO: 13:

CATGGTGTCG GTAGAAGCCT TACCACGGTA GAAGTGACCG TTACCTTCGT AGCAAGTTTT      60

GCTCA                                                                 65

(2) INFORMATION FOR SEQ ID NO: 14:

(i) SEQUENCE CHARACTERISTICS:
         (A) LENGTH: 83 base pairs
         (B) TYPE: nucleic acid
         (C) STRANDEDNESS: single
         (D) TOPOLOGY: linear (ii) MOLECULE TYPE: other nucleic acid
         (A) DESCRIPTION:  /desc = "Synthetic DNA;
             Nucleotide sequence for Oligo O220"

(iii) HYPOTHETICAL: NO (iv) ANTI-SENSE: NO (xi) SEQUENCE DESCRIPTION: SEQ ID NO: 14:
```

```
CGGTTAAGGC TTTCCCGAGG CCTGGTGGTG GTGGTAACGG TGACTTCGAA GAAATCCCGG      60

AAGAGTACCT GTGATAGGAT CAA                                             83
```

(2) INFORMATION FOR SEQ ID NO: 15:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O221"

(iii) HYPOTHETICAL: NO (iv) ANTI-SENSE: NO (xi) SEQUENCE DESCRIPTION: SEQ ID NO: 15:

```
CTAGTTGATC CTATCACAGG TACTCTTCCG GGATTTCTTC GAAGTCACCG TTACCACCAC      60

CACCAGGCCT CGGGAAAGCC TTAACCGGGC T                                    91
```

(2) INFORMATION FOR SEQ ID NO: 16:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O265"

(iii) HYPOTHETICAL: NO (iv) ANTI-SENSE: NO (xi) SEQUENCE DESCRIPTION: SEQ ID NO: 16:

```
CACCCGGCGG AGACGGCGGG CTCAGAGCCA GACCGTTTTC TTCTTTGGTG TGAGAACG       58
```

(2) INFORMATION FOR SEQ ID NO: 17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O27-1"

(iii) HYPOTHETICAL: NO (iv) ANTI-SENSE: NO (xi) SEQUENCE DESCRIPTION: SEQ ID NO: 17:

```
TATGAGTAGT CCACCAGAAG AGCT                                            24
```

(2) INFORMATION FOR SEQ ID NO: 18:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "Synthetic DNA;
            Nucleotide sequence for Oligo O27-2"

(iii) HYPOTHETICAL: NO (iv) ANTI-SENSE: NO (xi) SEQUENCE DESCRIPTION: SEQ ID NO: 18:

GAGCTCTTCT GGTGGACTAC TCA                                                23

(2) INFORMATION FOR SEQ ID NO: 19:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O281"

(iii) HYPOTHETICAL: NO (iv) ANTI-SENSE: NO (xi) SEQUENCE DESCRIPTION: SEQ ID NO: 19:

CGTCCGGGTG GTGGTGGTAA CGGTGACTTC GAAGAAATCC CGGAAGAATA CCTGTAAG      58

(2) INFORMATION FOR SEQ ID NO: 20:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O282"

(iii) HYPOTHETICAL: NO (iv) ANTI-SENSE: NO (xi) SEQUENCE DESCRIPTION: SEQ ID NO: 20:

GATCCGTTCT CACACCAAAG AAGAAAACGG TCTGGCTCTG AGCCCGCCGT CTCCGCCGGG    60

TGGTTTCCCG                                                            70

(2) INFORMATION FOR SEQ ID NO: 21:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O283"

(iii) HYPOTHETICAL: NO (iv) ANTI-SENSE: NO (xi) SEQUENCE DESCRIPTION: SEQ ID NO: 21:

CTAGCTTACA GGTATTCTTC CGGGATTTCT TCGAAGTCAC CGTTACCACC ACCACCCGGA    60

CGCGGGAAAC                                                            70

(2) INFORMATION FOR SEQ ID NO: 22:

(i) SEQUENCE CHARACTERISTICS:
    (A) LENGTH: 57 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "Synthetic DNA;
        Nucleotide sequence for Oligo O306"

(iii) HYPOTHETICAL: NO (iv) ANTI-SENSE: NO (xi) SEQUENCE DESCRIPTION: SEQ ID NO: 22:

ACGTAACCCG AATGACAAAT ACGAACCGTT CTGGGAAGAT GAAGAGAAAG GGCCCCA         57

(2) INFORMATION FOR SEQ ID NO: 23:

(i) SEQUENCE CHARACTERISTICS:
    (A) LENGTH: 55 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "Synthetic DNA;
        Nucleotide sequence for Oligo O307"

(iii) HYPOTHETICAL: NO (iv) ANTI-SENSE: NO (xi) SEQUENCE DESCRIPTION: SEQ ID NO: 23:

CTAGATAAGG AGGAAATAAT ATGAGCAATG AACTTGACCC GCGTCCGTTC CTGCT           55

(2) INFORMATION FOR SEQ ID NO: 24:

(i) SEQUENCE CHARACTERISTICS:
    (A) LENGTH: 65 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "Synthetic DNA,
        Nucleotide sequence for Oligo O308"

(iii) HYPOTHETICAL: NO (iv) ANTI-SENSE: NO (xi) SEQUENCE DESCRIPTION: SEQ ID NO: 24:

CATTCGGGTT ACGTAGCAGG AACGGACGCG GGTCAAGTTC ATTGCTCATA TTATTTCCTC      60

CTTAT                                                                 65

(2) INFORMATION FOR SEQ ID NO: 25:

(i) SEQUENCE CHARACTERISTICS:
    (A) LENGTH: 45 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "Synthetic DNA;
        Nucleotide sequence for Oligo O309"

(iii) HYPOTHETICAL: NO (iv) ANTI-SENSE: NO (xi) SEQUENCE DESCRIPTION: SEQ ID NO: 25:

TATGGGGCCC TTTCTCTTCA TCTTCCCAGA ACGGTTCGTA TTTGT                    45

(2) INFORMATION FOR SEQ ID NO: 26:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O329"

(iii) HYPOTHETICAL: NO (iv) ANTI-SENSE: NO (xi) SEQUENCE DESCRIPTION: SEQ ID NO: 26:

AAGAAATCCC GGAAGAATAC CTGCAATAAG                                     30

(2) INFORMATION FOR SEQ ID NO: 27:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O330"

(iii) HYPOTHETICAL: NO (iv) ANTI-SENSE: NO (xi) SEQUENCE DESCRIPTION: SEQ ID NO: 27:

CGGTTAAGGC TTGGGGACCG CGGCCGCTGG GTGGTGGTGG TAACGGTGAC TTCG          54

(2) INFORMATION FOR SEQ ID NO: 28:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O331"

(iii) HYPOTHETICAL: NO (iv) ANTI-SENSE: NO (xi) SEQUENCE DESCRIPTION: SEQ ID NO: 28:

ACCACCACCC AGCGGCCGCG GTCCCCAAGC CTTAACCGGG CT                       42

(2) INFORMATION FOR SEQ ID NO: 29:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O332"

(iii) HYPOTHETICAL: NO (iv) ANTI-SENSE: NO (xi) SEQUENCE DESCRIPTION: SEQ ID NO: 29:

CTAGCTTATT GCAGGTATTC TTCCGGGATT TCTTCGAAGT CACCGTTACC                50

(2) INFORMATION FOR SEQ ID NO: 30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O347"

(iii) HYPOTHETICAL: NO (iv) ANTI-SENSE: NO (xi) SEQUENCE DESCRIPTION: SEQ ID NO: 30:

CGGTTGTTGC TTTCCCGC                                                  18

(2) INFORMATION FOR SEQ ID NO: 31:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O348"

(iii) HYPOTHETICAL: NO (iv) ANTI-SENSE: NO (xi) SEQUENCE DESCRIPTION: SEQ ID NO: 31:

GGCCGCGGGA AAGCAACAAC CGGGCT                                         26

(2) INFORMATION FOR SEQ ID NO: 32:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O572"

(iii) HYPOTHETICAL: NO (iv) ANTI-SENSE: NO (xi) SEQUENCE DESCRIPTION: SEQ ID NO: 32:

CATGGTGTCG GTAGAAGCCT TACCACGGTA GAAGTGGCCG TTACCTTCGT AGCAAGTTTT     60
A                                                                    61

(2) INFORMATION FOR SEQ ID NO: 33:

(i) SEQUENCE CHARACTERISTICS:
        (A) LENGTH: 57 base pairs
        (B) TYPE: nucleic acid
        (C) STRANDEDNESS: single (D) TOPOLOGY: linear (ii) MOLECULE TYPE: other nucleic acid
        (A) DESCRIPTION: /desc = "Synthetic DNA;
            Nucleotide sequence for Oligo O573"

(iii) HYPOTHETICAL: NO (iv) ANTI-SENSE: NO (xi) SEQUENCE DESCRIPTION: SEQ ID NO: 33:

GAGATCTGCA GGTATTCTTC CGGGATTTCT TCGAAGTCAC CGTCGTTGTG AGATTCC        57

(2) INFORMATION FOR SEQ ID NO: 34:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence fur Oligo O574"

(iii) HYPOTHETICAL: NO (iv) ANTI-SENSE: NO (xi) SEQUENCE DESCRIPTION: SEQ ID NO: 34:

GGTTTCGGAG TACCTTCACC AGTAACGACC TGGTTACCTT TACCGTCG        48

(2) INFORMATION FOR SEQ ID NO: 35:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O575"

(iii) HYPOTHETICAL: NO (iv) ANTI-SENSE: NO (xi) SEQUENCE DESCRIPTION: SEQ ID NO: 35:

GATCCGACGG TAAAGGTAAC CAGTGCGTTA CTGGTGAAGG TACTCCGAAA CCGGAATCTC        60

ACAACGACG        69

(2) INFORMATION FOR SEQ ID NO: 36:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O576"

(iii) HYPOTHETICAL: NO (iv) ANTI-SENSE: NO (xi) SEQUENCE DESCRIPTION: SEQ ID NO: 36:

GCCACTTCTA CCGTGGTAAG GCTTCTACCG ACAC        34

(2) INFORMATION FOR SEQ ID NO: 37:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O577"

(iii) HYPOTHETICAL: NO (iv) ANTI-SENSE: NO (xi) SEQUENCE DESCRIPTION: SEQ ID NO: 37:

GTGACTTCGA AGAAATCCCG GAAGAATACC TGCAGATCTC TAAAACTTGC TACGAAGGTA     60

ACG     63

(2) INFORMATION FOR SEQ ID NO: 38:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O583"

(iii) HYPOTHETICAL: NO (iv) ANTI-SENSE: NO (xi) SEQUENCE DESCRIPTION: SEQ ID NO: 38:

GCAAACGTTA GAACCTTCGC ACAGGCACAG GTTCTGACCA GATTCAGTGC AGTCAGTGTA     60

CGTAATCA     68

(2) INFORMATION FOR SEQ ID NO: 39:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O584"

(iii) HYPOTHETICAL: NO (iv) ANTI-SENSE: NO (xi) SEQUENCE DESCRIPTION: SEQ ID NO: 39:

GATCCCAGGA TGCATTTGTT ACCTTTACC     29

(2) INFORMATION FOR SEQ ID NO: 40:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O585"

(iii) HYPOTHETICAL: NO (iv) ANTI-SENSE: NO (xi) SEQUENCE DESCRIPTION: SEQ ID NO: 40:

GAAGGTTCTA ACGTTTGCGG TAAAGGTAAC AAATGCATCC TGG                     43

(2) INFORMATION FOR SEQ ID NO: 41:

(i) SEQUENCE CHARACTERISTICS:
            (A) LENGTH: 52 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic DNA;
                Nucleotide sequence for Oligo O586"

(iii) HYPOTHETICAL: NO (iv) ANTI-SENSE: NO (xi) SEQUENCE DESCRIPTION: SEQ ID NO: 41:

TATGATTACG TACACTGACT GCACTGAATC TGGTCAGAAC CTGTGCCTGT GC           52

(2) INFORMATION FOR SEQ ID NO: 42:

(i) SEQUENCE CHARACTERISTICS:
            (A) LENGTH: 63 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic DNA;
                Nucleotide sequence for Oligo O616"

(iii) HYPOTHETICAL: NO (iv) ANTI-SENSE: NO (xi) SEQUENCE DESCRIPTION: SEQ ID NO: 42:

CTAGCTTATT GTTCAATGTC GTCCAGAGAG AATTCTTCGA AGTCGCTCGG ACCACCACCA   60

CCC                                                                63

(2) INFORMATION FOR SEQ ID NO: 43:

(i) SEQUENCE CHARACTERISTICS:
            (A) LENGTH: 63 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic DNA,
                Nucleotide sequence for Oligo O617"

(iii) HYPOTHETICAL: NO (iv) ANTI-SENSE: NO (xi) SEQUENCE DESCRIPTION: SEQ ID NO: 43:

GGCCGGGTGG TGGTGGTCCG AGCGACTTCG AAGAATTCTC TCTGGACGAC ATTGAACAAT   60

AAG                                                                63

(2) INFORMATION FOR SEQ ID NO: 44:

(i) SEQUENCE CHARACTERISTICS:
            (A) LENGTH: 393 amino acids
            (B) TYPE: amino acid -continued

```
      (C) STRANDEDNESS:
      (D) TOPOLOGY: linear (ii) MOLECULE TYPE: protein (xi) SEQUENCE DESCRIPTION: SEQ ID NO: 44:

Met Ser Lys Thr Cys Tyr Glu Gly Asn Gly His Phe Tyr Arg Gly Lys
1               5                   10                  15

Ala Ser Thr Asp Thr Met Gly Arg Pro Cys Leu Pro Trp Asn Ser Ala
            20                  25                  30

Thr Val Leu Gln Gln Thr Tyr His Ala His Arg Ser Asp Ala Leu Gln
        35                  40                  45

Leu Gly Leu Gly Lys His Asn Tyr Cys Arg Asn Pro Asp Asn Arg Arg
    50                  55                  60

Arg Pro Trp Cys Tyr Val Gln Val Gly Leu Lys Pro Leu Val Gln Glu
65                  70                  75                  80

Cys Met Val His Asp Cys Ala Asp Gly Lys Lys Pro Ser Ser Pro Pro
                85                  90                  95

Glu Glu Leu Lys Phe Gln Cys Gly Gln Lys Thr Leu Arg Pro Arg Phe
            100                 105                 110

Lys Ile Ile Gly Gly Glu Phe Thr Thr Ile Glu Asn Gln Pro Trp Phe
        115                 120                 125

Ala Ala Ile Tyr Arg Arg His Arg Gly Gly Ser Val Thr Tyr Val Cys
    130                 135                 140

Gly Gly Ser Leu Ile Ser Pro Cys Trp Val Ile Ser Ala Thr His Cys
145                 150                 155                 160

Phe Ile Asp Tyr Pro Lys Lys Glu Asp Tyr Ile Val Tyr Leu Gly Arg
                165                 170                 175

Ser Arg Leu Asn Ser Asn Thr Gln Gly Glu Met Lys Phe Glu Val Glu
            180                 185                 190

Asn Leu Ile Leu His Lys Asp Tyr Ser Ala Asp Thr Leu Ala His His
        195                 200                 205

Asn Asp Ile Ala Leu Leu Lys Ile Arg Ser Lys Glu Gly Arg Cys Ala
    210                 215                 220

Gln Pro Ser Arg Thr Ile Gln Thr Ile Cys Leu Pro Ser Met Tyr Asn
225                 230                 235                 240

Asp Pro Gln Phe Gly Thr Ser Cys Glu Ile Thr Gly Phe Gly Lys Glu
                245                 250                 255

Asn Ser Thr Asp Tyr Leu Tyr Pro Glu Gln Leu Lys Met Thr Val Val
            260                 265                 270

Lys Leu Ile Ser His Arg Glu Cys Gln Gln Pro His Tyr Tyr Gly Ser
        275                 280                 285

Glu Val Thr Thr Lys Met Leu Cys Ala Ala Asp Pro Gln Trp Lys Thr
    290                 295                 300

Asp Ser Cys Gln Gly Asp Ser Gly Gly Pro Leu Val Cys Ser Leu Gln
305                 310                 315                 320

Gly Arg Met Thr Leu Thr Gly Ile Val Ser Trp Gly Arg Gly Cys Ala
                325                 330                 335

Leu Lys Asp Lys Pro Gly Val Tyr Thr Arg Val Ser His Phe Leu Pro
            340                 345                 350

Trp Ile Arg Ser His Thr Lys Glu Glu Asn Gly Leu Ala Leu Ser Pro
        355                 360                 365

Val Val Ala Phe Pro Arg Pro Gly Gly Gly Pro Ser Asp Phe Glu
    370                 375                 380

Glu Phe Ser Leu Asp Asp Ile Glu Gln
```

-continued

```
           385                 390
```

(2) INFORMATION FOR SEQ ID NO: 45:

(i) SEQUENCE CHARACTERISTICS:
        (A) LENGTH: 306 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 45:

```
Met Ser Asn Glu Leu Asp Pro Arg Pro Phe Leu Leu Arg Asn Pro Asn
 1               5                  10                  15

Asp Lys Tyr Glu Pro Phe Trp Glu Asp Glu Lys Gly Pro His Met
            20                  25                  30

Ser Ser Pro Pro Glu Glu Leu Lys Phe Gln Cys Gly Gln Lys Thr Leu
        35                  40                  45

Arg Pro Arg Phe Lys Ile Ile Gly Gly Glu Phe Thr Thr Ile Glu Asn
    50                  55                  60

Gln Pro Trp Phe Ala Ala Ile Tyr Arg Arg His Arg Gly Gly Ser Val
65                  70                  75                  80

Thr Tyr Val Cys Gly Gly Ser Leu Ile Ser Pro Cys Trp Val Ile Ser
                85                  90                  95

Ala Thr His Cys Phe Ile Asp Tyr Pro Lys Lys Glu Asp Tyr Ile Val
            100                 105                 110

Tyr Leu Gly Arg Ser Arg Leu Asn Ser Asn Thr Gln Gly Glu Met Lys
        115                 120                 125

Phe Glu Val Glu Asn Leu Ile Leu His Lys Asp Tyr Ser Ala Asp Thr
    130                 135                 140

Leu Ala His His Asn Asp Ile Ala Leu Leu Lys Ile Arg Ser Lys Glu
145                 150                 155                 160

Gly Arg Cys Ala Gln Pro Ser Arg Thr Ile Gln Thr Ile Cys Leu Pro
                165                 170                 175

Ser Met Tyr Asn Asp Pro Gln Phe Gly Thr Ser Cys Glu Ile Thr Gly
            180                 185                 190

Phe Gly Lys Glu Asn Ser Thr Asp Tyr Leu Tyr Pro Glu Gln Leu Lys
        195                 200                 205

Met Thr Val Val Lys Leu Ile Ser His Arg Glu Cys Gln Gln Pro His
    210                 215                 220

Tyr Tyr Gly Ser Glu Val Thr Thr Lys Met Leu Cys Ala Ala Asp Pro
225                 230                 235                 240

Gln Trp Lys Thr Asp Ser Cys Gln Gly Asp Ser Gly Gly Pro Leu Val
                245                 250                 255

Cys Ser Leu Gln Gly Arg Met Thr Leu Thr Gly Ile Val Ser Trp Gly
            260                 265                 270

Arg Gly Cys Ala Leu Lys Asp Lys Pro Gly Val Tyr Thr Arg Val Ser
        275                 280                 285

His Phe Leu Pro Trp Ile Arg Ser His Thr Lys Glu Glu Asn Gly Leu
    290                 295                 300

Ala Leu
305
```

(2) INFORMATION FOR SEQ ID NO: 46:

(i) SEQUENCE CHARACTERISTICS:
        (A) LENGTH: 331 amino acids (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 46:

Met Ser Asn Glu Leu Asp Pro Arg Pro Phe Leu Leu Arg Asn Pro Asn
    1               5                  10                  15

Asp Lys Tyr Glu Pro Phe Trp Glu Asp Glu Lys Gly Pro His Met
                20                  25                  30

Ser Ser Pro Pro Glu Glu Leu Lys Phe Gln Cys Gly Gln Lys Thr Leu
            35                  40                  45

Arg Pro Arg Phe Lys Ile Ile Gly Gly Glu Phe Thr Thr Ile Glu Asn
    50                  55                  60

Gln Pro Trp Phe Ala Ala Ile Tyr Arg Arg His Arg Gly Gly Ser Val
    65                  70                  75                  80

Thr Tyr Val Cys Gly Gly Ser Leu Ile Ser Pro Cys Trp Val Ile Ser
                    85                  90                  95

Ala Thr His Cys Phe Ile Asp Tyr Pro Lys Lys Glu Asp Tyr Ile Val
                    100                 105                 110

Tyr Leu Gly Arg Ser Arg Leu Asn Ser Asn Thr Gln Gly Glu Met Lys
                    115                 120                 125

Phe Glu Val Glu Asn Leu Ile Leu His Lys Asp Tyr Ser Ala Asp Thr
    130                 135                 140

Leu Ala His His Asn Asp Ile Ala Leu Leu Lys Ile Arg Ser Lys Glu
    145                 150                 155                 160

Gly Arg Cys Ala Gln Pro Ser Arg Thr Ile Gln Thr Ile Cys Leu Pro
                    165                 170                 175

Ser Met Tyr Asn Asp Pro Gln Phe Gly Thr Ser Cys Glu Ile Thr Gly
                    180                 185                 190

Phe Gly Lys Glu Asn Ser Thr Asp Tyr Leu Tyr Pro Glu Gln Leu Lys
                    195                 200                 205

Met Thr Val Val Lys Leu Ile Ser His Arg Glu Cys Gln Gln Pro His
    210                 215                 220

Tyr Tyr Gly Ser Glu Val Thr Thr Lys Met Leu Cys Ala Ala Asp Pro
    225                 230                 235                 240

Gln Trp Lys Thr Asp Ser Cys Gln Gly Asp Ser Gly Gly Pro Leu Val
                    245                 250                 255

Cys Ser Leu Gln Gly Arg Met Thr Leu Thr Gly Ile Val Ser Trp Gly
                    260                 265                 270

Arg Gly Cys Ala Leu Lys Asp Lys Pro Gly Val Tyr Thr Arg Val Ser
                    275                 280                 285

His Phe Leu Pro Trp Ile Arg Ser His Thr Lys Glu Glu Asn Gly Leu
                    290                 295                 300

Ala Leu Ser Pro Val Lys Ala Phe Pro Arg Pro Gly Gly Gly Gly Asn
    305                 310                 315                 320

Gly Asp Phe Glu Glu Ile Pro Glu Glu Tyr Leu
                    325                 330

(2) INFORMATION FOR SEQ ID NO: 47:

(i) SEQUENCE CHARACTERISTICS:
        (A) LENGTH: 432 amino acids
        (B) TYPE: amino acid
        (C) STRANDEDNESS:
        (D) TOPOLOGY: linear -continued (ii) MOLECULE TYPE: protein (xi) SEQUENCE DESCRIPTION: SEQ ID NO: 47:

```
Met Ile Thr Tyr Thr Asp Cys Thr Glu Ser Gly Gln Asn Leu Cys Leu
 1               5                  10                  15

Cys Glu Gly Ser Thr Val Cys Gly Lys Gly Asn Lys Cys Ile Leu Gly
            20                  25                  30

Ser Asn Gly Lys Gly Asn Gln Cys Val Thr Gly Glu Gly Thr Pro Lys
        35                  40                  45

Pro Glu Ser His Asn Asn Gly Asp Phe Glu Glu Ile Pro Glu Glu Tyr
    50                  55                  60

Leu Gln Ile Ser Lys Thr Cys Tyr Glu Gly Asn Gly His Phe Tyr Arg
65                  70                  75                  80

Gly Lys Ala Ser Thr Asp Thr Met Gly Arg Pro Cys Leu Pro Trp Asn
                85                  90                  95

Ser Ala Thr Val Leu Gln Gln Thr Tyr His Ala His Arg Ser Asp Ala
            100                 105                 110

Leu Gln Leu Gly Leu Gly Lys His Asn Tyr Cys Arg Asn Pro Asp Asn
        115                 120                 125

Arg Arg Arg Pro Trp Cys Tyr Val Gln Val Gly Leu Lys Pro Leu Val
130                 135                 140

Gln Glu Cys Met Val His Asp Cys Ala Asp Gly Lys Lys Pro Ser Ser
145                 150                 155                 160

Pro Pro Glu Glu Leu Lys Phe Gln Cys Gly Gln Lys Thr Leu Arg Pro
                165                 170                 175

Arg Phe Lys Ile Ile Gly Gly Glu Phe Thr Thr Ile Glu Asn Gln Pro
            180                 185                 190

Trp Phe Ala Ala Ile Tyr Arg Arg His Arg Gly Gly Ser Val Thr Tyr
        195                 200                 205

Val Cys Gly Gly Ser Leu Ile Ser Pro Cys Trp Val Ile Ser Ala Thr
210                 215                 220

His Cys Phe Ile Asp Tyr Pro Lys Lys Glu Asp Tyr Ile Val Tyr Leu
225                 230                 235                 240

Gly Arg Ser Arg Leu Asn Ser Asn Thr Gln Gly Glu Met Lys Phe Glu
                245                 250                 255

Val Glu Asn Leu Ile Leu His Lys Asp Tyr Ser Ala Asp Thr Leu Ala
            260                 265                 270

His His Asn Asp Ile Ala Leu Leu Lys Ile Arg Ser Lys Glu Gly Arg
        275                 280                 285

Cys Ala Gln Pro Ser Arg Thr Ile Gln Thr Ile Cys Leu Pro Ser Met
290                 295                 300

Tyr Asn Asp Pro Gln Phe Gly Thr Ser Cys Glu Ile Thr Gly Phe Gly
305                 310                 315                 320

Lys Glu Asn Ser Thr Asp Tyr Leu Tyr Pro Glu Gln Leu Lys Met Thr
                325                 330                 335

Val Val Lys Leu Ile Ser His Arg Glu Cys Gln Gln Pro His Tyr Tyr
            340                 345                 350

Gly Ser Glu Val Thr Thr Lys Met Leu Cys Ala Ala Asp Pro Gln Trp
        355                 360                 365

Lys Thr Asp Ser Cys Gln Gly Asp Ser Gly Gly Pro Leu Val Cys Ser
370                 375                 380

Leu Gln Gly Arg Met Thr Leu Thr Gly Ile Val Ser Trp Gly Arg Gly
385                 390                 395                 400

Cys Ala Leu Lys Asp Lys Pro Gly Val Tyr Thr Arg Val Ser His Phe
```

```
                    405                 410                 415
    Leu Pro Trp Ile Arg Ser His Thr Lys Glu Glu Asn Gly Leu Ala Leu
                420                 425                 430

(2) INFORMATION FOR SEQ ID NO:48:

(i) SEQUENCE CHARACTERISTICS:
        (A) LENGTH: 411 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:48:

Ser Asn Glu Leu His Gln Val Pro Ser Asn Cys Asp Cys Leu Asn Gly
    1               5                  10                  15

Gly Thr Cys Val Ser Asn Lys Tyr Phe Ser Asn Ile His Trp Cys Asn
                    20                  25                  30

Cys Pro Lys Lys Phe Gly Gly Gln His Cys Glu Ile Asp Lys Ser Lys
                35                  40                  45

Thr Cys Tyr Glu Gly Asn Gly His Phe Tyr Arg Gly Lys Ala Ser Thr
                50                  55                  60

Asp Thr Met Gly Arg Pro Cys Leu Pro Trp Asn Ser Ala Thr Val Leu
    65                  70                  75                  80

Gln Gln Thr Tyr His Ala His Arg Ser Asp Ala Leu Gln Leu Gly Leu
                    85                  90                  95

Gly Lys His Asn Tyr Cys Arg Asn Pro Asp Asn Arg Arg Arg Pro Trp
                    100                 105                 110

Cys Tyr Val Gln Val Gly Leu Lys Pro Leu Val Gln Glu Cys Met Val
                    115                 120                 125

His Asp Trp Ala Asp Gly Lys Lys Pro Ser Ser Pro Pro Glu Glu Leu
                130                 135                 140

Lys Phe Gln Cys Gly Gln Lys Thr Leu Arg Pro Arg Phe Lys Ile Ile
    145                 150                 155                 160

Gly Gly Glu Phe Thr Thr Ile Glu Asn Gln Pro Trp Phe Ala Ala Ile
                    165                 170                 175

Tyr Arg Arg His Arg Gly Gly Ser Val Thr Tyr Val Cys Gly Gly Ser
                    180                 185                 190

Leu Ile Ser Pro Cys Trp Val Ile Ser Ala Thr His Cys Phe Ile Asp
                    195                 200                 205

Tyr Pro Lys Lys Glu Asp Tyr Ile Val Tyr Leu Gly Arg Ser Arg Leu
                210                 215                 220

Asn Ser Asn Thr Gln Gly Glu Met Lys Phe Glu Val Glu Asn Leu Ile
    225                 230                 235                 240

Leu His Lys Asp Tyr Ser Ala Asp Thr Leu Ala His His Asn Asp Ile
                    245                 250                 255

Ala Leu Leu Lys Ile Arg Ser Lys Glu Gly Arg Cys Ala Gln Pro Ser
                    260                 265                 270

Arg Thr Ile Gln Thr Ile Cys Leu Pro Ser Met Tyr Asn Asp Pro Gln
                    275                 280                 285

Phe Gly Thr Ser Cys Glu Ile Thr Gly Phe Gly Lys Glu Asn Ser Thr
                    290                 295                 300

Asp Tyr Leu Tyr Pro Glu Gln Leu Lys Met Thr Val Val Lys Leu Ile
    305                 310                 315                 320

Ser His Arg Glu Cys Gln Gln Pro His Tyr Tyr Gly Ser Glu Val Thr
                    325                 330                 335
```

```
        Thr Lys Met Leu Cys Ala Ala Asp Pro Gln Trp Lys Thr Asp Ser Cys
                    340                 345                 350

Gln Gly Asp Ser Gly Gly Pro Leu Val Cys Ser Leu Gln Cys Arg Met
                    355                 360                 365

Thr Leu Thr Gly Ile Val Ser Trp Gly Arg Gly Cys Ala Leu Lys Asp
                    370                 375                 380

Lys Pro Gly Val Tyr Thr Arg Val Ser His Phe Leu Pro Trp Ile Arg
        385                 390                 395                 400

Ser His Thr Lys Glu Glu Asn Gly Leu Val Leu
                    405                 410

(2) INFORMATION FOR SEQ ID NO:49:

(i) SEQUENCE CHARACTERISTICS:
        (A) LENGTH: 254 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:49:

Lys Ile Ile Gly Gly Glu Phe Thr Thr Ile Glu Asn Gln Pro Trp Phe
        1               5                   10                  15

Ala Ala Ile Tyr Arg Arg His Arg Gly Gly Ser Val Thr Tyr Val Cys
                    20                  25                  30

Gly Gly Ser Leu Ile Ser Pro Cys Trp Val Ile Ser Ala Thr His Cys
                    35                  40                  45

Phe Ile Asp Tyr Pro Lys Lys Glu Asp Tyr Ile Val Tyr Leu Gly Arg
        50                  55                  60

Ser Arg Leu Asn Ser Asn Thr Gln Gly Glu Met Lys Phe Glu Val Glu
        65                  70                  75                  80

Asn Leu Ile Leu His Lys Asp Tyr Ser Ala Asp Thr Leu Ala His His
                    85                  90                  95

Asn Asp Ile Ala Leu Leu Lys Ile Arg Ser Lys Glu Gly Arg Cys Ala
                    100                 105                 110

Gln Pro Ser Arg Thr Ile Gln Thr Ile Cys Leu Pro Ser Met Tyr Asn
                    115                 120                 125

Asp Pro Gln Phe Gly Thr Ser Cys Glu Ile Thr Gly Phe Gly Lys Glu
                    130                 135                 140

Asn Ser Thr Asp Tyr Leu Tyr Pro Glu Gln Leu Lys Met Thr Val Val
        145                 150                 155                 160

Lys Leu Ile Ser His Arg Glu Cys Gln Gln Pro His Tyr Tyr Gly Ser
                    165                 170                 175

Glu Val Thr Thr Lys Met Leu Cys Ala Ala Asp Pro Gln Trp Lys Thr
                    180                 185                 190

Asp Ser Cys Gln Gly Asp Ser Gly Gly Pro Leu Val Cys Ser Leu Gln
                    195                 200                 205

Cys Arg Met Thr Leu Thr Gly Ile Val Ser Trp Gly Arg Gly Cys Ala
                    210                 215                 220

Leu Lys Asp Lys Pro Gly Val Tyr Thr Arg Val Ser His Phe Leu Pro
        225                 230                 235                 240

Trp Ile Arg Ser His Thr Lys Glu Glu Asn Gly Leu Val Leu
                    245                 250

(2) INFORMATION FOR SEQ ID NO:50:
```

(i) SEQUENCE CHARACTERISTICS:
    (A) LENGTH: 562 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:50:

```
Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ala Arg Ser Tyr Gln Val Ile Cys Arg Asp Glu Lys Thr Gln Met
        35                  40                  45

Ile Tyr Gln Gln His Gln Ser Trp Leu Arg Pro Val Leu Arg Ser Asn
    50                  55                  60

Arg Val Glu Tyr Cys Trp Cys Asn Ser Gly Arg Ala Gln Cys His Ser
65                  70                  75                  80

Val Pro Val Lys Ser Cys Ser Glu Pro Arg Cys Phe Asn Gly Gly Thr
                85                  90                  95

Cys Gln Gln Ala Leu Tyr Phe Ser Asp Phe Val Cys Gln Cys Pro Glu
            100                 105                 110

Gly Phe Ala Gly Lys Cys Cys Glu Ile Asp Thr Arg Ala Thr Cys Tyr
        115                 120                 125

Glu Asp Gln Gly Ile Ser Tyr Arg Gly Thr Trp Ser Thr Ala Glu Ser
    130                 135                 140

Gly Ala Glu Cys Thr Asn Trp Asn Ser Ser Ala Leu Ala Gln Lys Pro
145                 150                 155                 160

Tyr Ser Gly Arg Arg Pro Asp Ala Ile Arg Leu Gly Leu Gly Asn His
                165                 170                 175

Asn Tyr Cys Arg Asn Pro Asp Arg Asp Ser Lys Pro Trp Cys Tyr Val
            180                 185                 190

Phe Lys Ala Gly Lys Tyr Ser Ser Glu Phe Cys Ser Thr Pro Ala Cys
        195                 200                 205

Ser Glu Gly Asn Ser Asp Cys Tyr Phe Gly Asn Gly Ser Ala Tyr Arg
    210                 215                 220

Gly Thr His Ser Leu Thr Glu Ser Gly Ala Ser Cys Leu Pro Trp Asn
225                 230                 235                 240

Ser Met Ile Leu Ile Gly Lys Val Tyr Thr Ala Gln Asn Pro Ser Ala
                245                 250                 255

Gln Ala Leu Gly Leu Gly Lys His Asn Tyr Cys Arg Asn Pro Asp Gly
            260                 265                 270

Asp Ala Lys Pro Trp Cys His Val Leu Lys Asn Arg Arg Leu Thr Trp
        275                 280                 285

Glu Tyr Cys Asp Val Pro Ser Cys Ser Thr Cys Gly Leu Arg Gln Tyr
    290                 295                 300

Ser Gln Pro Gln Phe Arg Ile Lys Gly Gly Leu Phe Ala Asp Ile Ala
305                 310                 315                 320

Ser His Pro Trp Gln Ala Ala Ile Phe Ala Lys His Arg Arg Ser Pro
                325                 330                 335

Gly Glu Arg Phe Leu Cys Gly Gly Ile Leu Ile Ser Ser Cys Trp Ile
            340                 345                 350

Leu Ser Ala Ala His Cys Phe Gln Glu Arg Phe Pro Pro His His Leu
        355                 360                 365

Thr Val Ile Leu Gly Arg Thr Tyr Arg Val Val Pro Gly Glu Glu Glu
```

370                 375                 380
        Gln Lys Phe Glu Val Glu Lys Tyr Ile Val His Lys Glu Phe Asp Asp
        385                 390                 395                 400

Asp Thr Tyr Asp Asn Asp Ile Ala Leu Leu Gln Leu Lys Ser Asp Ser
                        405                 410                 415

Ser Arg Cys Ala Gln Glu Ser Ser Val Val Arg Thr Val Cys Leu Pro
                    420                 425                 430

Pro Ala Asp Leu Gln Leu Pro Asp Trp Thr Glu Cys Glu Leu Ser Gly
                        435                 440                 445

Tyr Gly Lys His Glu Ala Leu Ser Pro Phe Tyr Ser Glu Arg Leu Lys
                    450                 455                 460

Glu Ala His Val Arg Leu Tyr Pro Ser Ser Arg Cys Thr Ser Gln His
        465                 470                 475                 480

Leu Leu Asn Arg Thr Val Thr Asp Asn Met Leu Cys Ala Gly Asp Thr
                        485                 490                 495

Arg Ser Gly Gly Pro Gln Ala Asn Leu His Asp Ala Cys Gln Gly Asp
                    500                 505                 510

Ser Gly Gly Pro Leu Val Cys Leu Asn Asp Gly Arg Met Thr Leu Val
                    515                 520                 525

Gly Ile Ile Ser Trp Gly Leu Gly Cys Gly Gln Lys Asp Val Pro Gly
                    530                 535                 540

Val Tyr Thr Lys Val Thr Asn Tyr Leu Asp Trp Ile Arg Asp Asn Met
        545                 550                 555                 560

Arg Pro (2) INFORMATION FOR SEQ ID NO:51:

(i) SEQUENCE CHARACTERISTICS:
        (A) LENGTH: 477 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:51:

Met Val Asn Thr Met Lys Thr Lys Leu Leu Cys Val Leu Leu Leu Cys
        1               5                   10                  15

Gly Ala Val Phe Ser Leu Pro Arg Gln Glu Thr Tyr Arg Gln Leu Ala
                        20                  25                  30

Arg Gly Ser Arg Ala Tyr Gly Val Ala Cys Arg Asp Glu Lys Thr Gln
                    35                  40                  45

Met Ile Tyr Gln Gln Gln Glu Ser Trp Leu Arg Pro Glu Val Arg Ser
            50                  55                  60

Lys Arg Val Glu His Cys Arg Cys Asp Arg Gly Leu Ala Gln Cys His
        65                  70                  75                  80

Thr Val Pro Val Lys Ser Cys Ser Glu Leu Arg Cys Phe Asn Gly Gly
                        85                  90                  95

Thr Cys Trp Gln Ala Ala Ser Phe Ser Asp Phe Val Cys Gln Cys Pro
                    100                 105                 110

Lys Gly Tyr Thr Gly Lys Gln Cys Glu Val Asp Thr His Ala Thr Cys
                    115                 120                 125

Tyr Lys Asp Gln Gly Val Thr Tyr Arg Gly Thr Trp Ser Thr Ser Glu
            130                 135                 140

Ser Gly Ala Gln Cys Ile Asn Trp Asn Ser Asn Leu Leu Thr Arg Arg
        145                 150                 155                 160

```
Thr Tyr Asn Gly Arg Arg Ser Asp Ala Ile Thr Leu Gly Leu Gly Asn
                165                 170                 175

His Asn Tyr Cys Arg Asn Pro Asp Asn Asn Ser Lys Pro Trp Cys Tyr
                180                 185                 190

Val Ile Lys Ala Ser Lys Phe Ile Leu Glu Phe Cys Ser Val Pro Val
            195                 200                 205

Cys Ser Lys Ala Thr Cys Gly Leu Arg Lys Tyr Lys Glu Pro Gln Leu
    210                 215                 220

His Ser Thr Gly Gly Leu Phe Thr Asp Ile Thr Ser His Pro Trp Gln
225                 230                 235                 240

Ala Ala Ile Phe Ala Gln Asn Arg Arg Ser Ser Gly Glu Arg Phe Leu
                245                 250                 255

Cys Gly Gly Ile Leu Ile Ser Ser Cys Trp Val Leu Thr Ala Ala His
                260                 265                 270

Cys Phe Gln Glu Arg Tyr Pro Pro Gln His Leu Arg Val Val Leu Gly
            275                 280                 285

Arg Thr Tyr Arg Val Lys Pro Gly Lys Glu Gln Thr Phe Glu Val
        290                 295                 300

Glu Lys Cys Ile Val His Glu Glu Phe Asp Asp Thr Tyr Asn Asn
305                 310                 315                 320

Asp Ile Ala Leu Leu Gln Leu Lys Ser Gly Ser Pro Gln Cys Ala Gln
                325                 330                 335

Glu Ser Asp Ser Val Arg Ala Ile Cys Leu Pro Glu Ala Asn Leu Gln
                340                 345                 350

Leu Pro Asp Trp Thr Glu Cys Glu Leu Ser Gly Tyr Gly Lys His Lys
        355                 360                 365

Ser Ser Ser Pro Phe Tyr Ser Glu Gln Leu Lys Glu Gly His Val Arg
        370                 375                 380

Leu Tyr Pro Ser Ser Arg Cys Thr Ser Lys Phe Leu Phe Asn Lys Thr
385                 390                 395                 400

Val Thr Lys Asn Met Leu Cys Ala Gly Asp Thr Arg Ser Gly Glu Ile
                405                 410                 415

His Pro Asn Val His Asp Ala Cys Gln Gly Asp Ser Gly Gly Pro Leu
                420                 425                 430

Val Cys Arg Asn Asp Asn His Met Thr Leu Leu Gly Ile Ile Ser Trp
        435                 440                 445

Gly Val Gly Cys Gly Glu Lys Asp Ile Pro Gly Val Tyr Thr Lys Val
    450                 455                 460

Thr Asn Tyr Leu Gly Trp Ile Arg Asp Asn Met Arg Pro
465                 470                 475
```

(2) INFORMATION FOR SEQ ID NO:52:

(i) SEQUENCE CHARACTERISTICS:
        (A) LENGTH: 440 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:52:

```
Met Lys Asn Tyr Leu Ser Phe Gly Met Phe Ala Leu Leu Phe Ala Leu
1               5                   10                  15

Thr Phe Gly Thr Val Asn Ser Val Gln Ala Ile Ala Gly Pro Glu Trp
            20                  25                  30

Leu Leu Asp Arg Pro Ser Val Asn Asn Ser Gln Leu Val Val Ser Val
```

```
                35                  40                  45
Ala Gly Thr Val Glu Gly Thr Asn Gln Asp Ile Ser Leu Lys Phe Phe
    50                  55                  60

Glu Ile Asp Leu Thr Ser Arg Pro Ala His Gly Gly Lys Thr Glu Gln
 65                  70                  75                  80

Gly Leu Ser Pro Lys Ser Lys Pro Phe Ala Thr Asp Ser Gly Ala Met
                 85                  90                  95

Ser His Lys Leu Glu Lys Ala Asp Leu Leu Lys Ala Ile Gln Glu Gln
                100                 105                 110

Leu Ile Ala Asn Val His Ser Asn Asp Asp Tyr Phe Glu Val Ile Asp
            115                 120                 125

Phe Ala Ser Asp Ala Thr Ile Thr Asp Arg Asn Gly Lys Val Tyr Phe
    130                 135                 140

Ala Asp Lys Asp Gly Ser Val Thr Leu Pro Thr Gln Pro Val Gln Glu
145                 150                 155                 160

Phe Leu Leu Ser Gly His Val Arg Val Arg Pro Tyr Lys Glu Lys Pro
                165                 170                 175

Ile Gln Asn Gln Ala Lys Ser Val Asp Val Glu Tyr Thr Val Gln Phe
            180                 185                 190

Thr Pro Leu Asn Pro Asp Asp Asp Phe Arg Pro Gly Leu Lys Asp Thr
    195                 200                 205

Lys Leu Leu Lys Thr Leu Ala Ile Gly Asp Thr Ile Thr Ser Gln Glu
210                 215                 220

Leu Leu Ala Gln Ala Gln Ser Ile Leu Asn Lys Asn His Pro Gly Tyr
225                 230                 235                 240

Thr Ile Tyr Glu Arg Asp Ser Ser Ile Val Thr His Asp Asn Asp Ile
                245                 250                 255

Phe Arg Thr Ile Leu Pro Met Asp Gln Glu Phe Thr Tyr Arg Val Lys
            260                 265                 270

Asn Arg Glu Gln Ala Tyr Arg Ile Asn Lys Lys Ser Gly Leu Asn Glu
    275                 280                 285

Glu Ile Asn Asn Thr Asp Leu Ile Ser Glu Lys Tyr Tyr Val Leu Lys
290                 295                 300

Lys Gly Glu Lys Pro Tyr Asp Pro Phe Asp Arg Ser His Leu Lys Leu
305                 310                 315                 320

Phe Thr Ile Lys Tyr Val Asp Val Asp Thr Asn Glu Leu Leu Lys Ser
                325                 330                 335

Glu Gln Leu Leu Thr Ala Ser Glu Arg Asn Leu Asp Phe Arg Asp Leu
            340                 345                 350

Tyr Asp Pro Arg Asp Lys Ala Lys Leu Leu Tyr Asn Asn Leu Asp Ala
    355                 360                 365

Phe Gly Ile Met Asp Tyr Thr Leu Thr Gly Lys Val Glu Asp Asn His
370                 375                 380

Asp Asp Thr Asn Arg Ile Ile Thr Val Tyr Met Gly Lys Arg Pro Glu
385                 390                 395                 400

Gly Glu Asn Ala Ser Tyr His Leu Ala Tyr Asp Lys Asp Arg Tyr Thr
                405                 410                 415

Glu Glu Glu Arg Glu Val Tyr Ser Tyr Leu Arg Tyr Thr Gly Thr Pro
            420                 425                 430

Ile Pro Asp Asn Pro Asn Asp Lys
    435                 440

(2) INFORMATION FOR SEQ ID NO:53:
```

```
    (i) SEQUENCE CHARACTERISTICS:
        (A) LENGTH: 171 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:53:

Met Thr Lys Lys Val Ala Ile Ile Leu Ala Asn Glu Phe Glu Asp Ile
1               5                   10                  15

Glu Tyr Ser Ser Pro Lys Glu Ala Leu Glu Asn Ala Gly Phe Asn Thr
            20                  25                  30

Val Val Ile Gly Asp Thr Ala Asn Ser Glu Val Val Gly Lys His Gly
        35                  40                  45

Glu Lys Val Thr Val Asp Val Gly Ile Ala Glu Ala Lys Pro Glu Asp
    50                  55                  60

Tyr Asp Ala Leu Leu Ile Pro Gly Gly Phe Ser Pro Asp His Leu Arg
65                  70                  75                  80

Gly Asp Thr Glu Gly Arg Tyr Gly Thr Phe Ala Lys Tyr Phe Thr Lys
                85                  90                  95

Asn Asp Val Pro Thr Phe Ala Ile Cys His Gly Pro Gln Ile Leu Ile
            100                 105                 110

Asp Thr Asp Asp Leu Lys Gly Arg Thr Leu Thr Ala Val Leu Asn Val
        115                 120                 125

Arg Lys Asp Leu Ser Asn Ala Gly Ala His Val Val Asp Glu Ser Val
    130                 135                 140

Val Val Asp Asn Asn Ile Val Thr Ser Arg Val Pro Asp Asp Leu Asp
145                 150                 155                 160

Asp Phe Asn Arg Glu Ile Val Lys Gln Leu Gln
                165                 170

(2) INFORMATION FOR SEQ ID NO:54:

(i) SEQUENCE CHARACTERISTICS:
        (A) LENGTH: 149 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:54:

Met Lys Arg Ser Asp Arg Tyr Ser Asn Ser Asn Glu His Phe Glu His
1               5                   10                  15

Met Lys His Glu Pro His Tyr Asn Thr Tyr Tyr Gln Pro Val Gly Lys
            20                  25                  30

Pro Pro Lys Lys Lys Lys Ser Lys Arg Ile Leu Leu Lys Ile Leu Leu
        35                  40                  45

Thr Ile Leu Ile Ile Ile Ala Leu Phe Ile Gly Ile Met Tyr Phe Leu
    50                  55                  60

Ser Thr Arg Asp Asn Val Asp Glu Leu Arg Lys Ile Glu Asn Lys Ser
65                  70                  75                  80

Ser Phe Val Ser Ala Asp Asn Met Pro Glu Tyr Val Lys Gly Ala Phe
                85                  90                  95

Ile Ser Met Glu Asp Glu Arg Phe Tyr Asn His His Gly Phe Asp Leu
            100                 105                 110

Lys Gly Thr Thr Arg Ala Leu Phe Ser Thr Ile Ser Asp Arg Asp Val
        115                 120                 125
```

```
    Gln Gly Gly Ser Thr Ile Thr Gln Gln Val Val Lys Asn Tyr Phe Tyr
        130                 135                 140

Asp Asn Asp Arg Leu
    145
```

(2) INFORMATION FOR SEQ ID NO:55:

(i) SEQUENCE CHARACTERISTICS:
        (A) LENGTH: 291 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:55:

```
    Met Tyr Tyr Ser Tyr Gly Asn Tyr Glu Ala Phe Ala Arg Pro Lys Lys
    1               5                   10                  15

Pro Glu Asn Val Glu Asn Lys Ser Ala Tyr Leu Ile Gly Ser Gly Leu
                20                  25                  30

Ala Ser Leu Ala Ala Ala Cys Phe Leu Ile Arg Asp Gly Gln Met Glu
            35                  40                  45

Gly Ser Lys Ile His Ile Leu Glu Glu Leu Pro Lys Ala Gly Gly Ser
        50                  55                  60

Leu Asp Gly Glu Asn Met Pro Leu Lys Gly Tyr Val Val Arg Gly Gly
    65                  70                  75                  80

Arg Glu Met Glu Asn His Phe Glu Cys Leu Trp Asp Leu Phe Arg Ser
                    85                  90                  95

Ile Pro Ser Leu Glu Ile Asp Asn Ala Ser Val Leu Asp Glu Phe Tyr
                    100                 105                 110

Trp Leu Asn Lys Glu Asp Pro Asn Tyr Ser Arg Cys Arg Val Ile Glu
                    115                 120                 125

Lys Gln Gly Gln Arg Leu Val Thr Asp Gly Asp Phe Thr Leu Thr Lys
        130                 135                 140

Thr Ala Ile Lys Glu Ile Leu Asp Leu Cys Leu Thr Asn Glu Glu Asp
    145                 150                 155                 160

Leu Asp Asp Val Lys Ile Thr Asp Val Phe Ser Asp Phe Phe Asn
                        165                 170                 175

Ser Asn Phe Trp Ile Tyr Trp Lys Thr Met Phe Ala Phe Glu Pro Trp
                    180                 185                 190

His Ser Ala Met Glu Met Arg Arg Tyr Leu Met Arg Phe Val His His
                    195                 200                 205

Ile Ser Gly Leu Ala Asp Phe Ser Ala Leu Lys Phe Thr Lys Tyr Asn
        210                 215                 220

Gln Tyr Glu Ser Leu Val Leu Pro Met Val Glu Tyr Leu Lys Ser His
    225                 230                 235                 240

Gly Val Gln Phe Glu Tyr Asp Val Lys Val Glu Asp Ile Lys Ile Asp
                    245                 250                 255

Val Thr Thr Ser Gln Lys Ile Ala Arg Glu Ile Leu Ile Asp Arg Asn
                    260                 265                 270

Gly Asn Ala Glu Ser Ile Lys Leu Thr Ile Asn Asp His Tyr His Lys
                275                 280                 285

Asn Asn Phe
        290
```

(2) INFORMATION FOR SEQ ID NO:56:

(i) SEQUENCE CHARACTERISTICS:

(A) LENGTH: 72 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:56:

Ala Ile Cys Val Ser Gln Ala Ile Thr Tyr Thr Asp Cys Thr Glu Ser
1               5                   10                  15

Gly Gln Asn Leu Cys Leu Cys Glu Gly Ser Asn Val Cys Gly Lys Gly
            20                  25                  30

Asn Lys Cys Ile Leu Gly Ser Asn Gly Lys Gly Asn Gln Cys Val Thr
        35                  40                  45

Gly Glu Gly Thr Pro Asn Pro Glu Ser His Asn Asn Gly Asp Phe Glu
    50                  55                  60

Glu Ile Pro Glu Glu Tyr Leu Gln
65                  70

(2) INFORMATION FOR SEQ ID NO:57:

(i) SEQUENCE CHARACTERISTICS:
        (A) LENGTH: 425 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:57:

Met Gly Pro Arg Arg Leu Leu Val Ala Ala Cys Phe Ser Leu Cys
1               5                   10                  15

Gly Pro Leu Leu Ser Ala Arg Thr Arg Ala Arg Arg Pro Glu Ser Lys
            20                  25                  30

Ala Thr Asn Ala Thr Leu Asp Pro Arg Ser Phe Leu Leu Arg Asn Pro
        35                  40                  45

Asn Asp Lys Tyr Glu Pro Phe Trp Glu Asp Glu Glu Lys Asn Glu Ser
    50                  55                  60

Gly Leu Thr Glu Tyr Arg Leu Val Ser Ile Asn Lys Ser Ser Pro Leu
65                  70                  75                  80

Gln Lys Gln Leu Pro Ala Phe Ile Ser Glu Asp Ala Ser Gly Tyr Leu
            85                  90                  95

Thr Ser Ser Trp Leu Thr Leu Phe Val Pro Ser Val Tyr Thr Gly Val
        100                 105                 110

Phe Val Val Ser Leu Pro Leu Asn Ile Met Ala Ile Val Val Phe Ile
    115                 120                 125

Leu Lys Met Lys Val Lys Lys Pro Ala Val Val Tyr Met Leu His Leu
130                 135                 140

Ala Thr Ala Asp Val Leu Phe Val Ser Val Leu Pro Phe Lys Ile Ser
145                 150                 155                 160

Tyr Tyr Phe Ser Gly Ser Asp Trp Gln Phe Gly Ser Glu Leu Cys Arg
            165                 170                 175

Phe Val Thr Ala Ala Phe Tyr Cys Asn Met Tyr Ala Ser Ile Leu Leu
        180                 185                 190

Met Thr Val Ile Ser Ile Asp Arg Phe Leu Ala Val Val Tyr Pro Met
    195                 200                 205

Gln Ser Leu Ser Trp Arg Thr Leu Gly Arg Ala Ser Phe Thr Cys Leu
210                 215                 220

Ala Ile Trp Ala Leu Ala Ile Ala Gly Val Val Pro Leu Val Leu Lys

```
              225                 230                 235                 240
    Glu Gln Thr Ile Gln Val Pro Gly Leu Asn Ile Thr Thr Cys His Asp
                        245                 250                 255

Val Leu Asn Glu Thr Leu Leu Glu Gly Tyr Tyr Ala Tyr Tyr Phe Ser
                260                 265                 270

Ala Phe Ser Ala Val Phe Phe Val Pro Leu Ile Ile Ser Thr Val
                275                 280                 285

Cys Tyr Val Ser Ile Ile Arg Cys Leu Ser Ser Ala Val Ala Asn
                290                 295                 300

Arg Ser Lys Lys Ser Arg Ala Leu Phe Leu Ser Ala Ala Val Phe Cys
    305                 310                 315                 320

Ile Phe Ile Ile Cys Phe Gly Pro Thr Asn Val Leu Leu Ile Ala His
                        325                 330                 335

Tyr Ser Phe Leu Ser His Thr Ser Thr Glu Ala Ala Tyr Phe Ala
                340                 345                 350

Tyr Leu Leu Cys Val Cys Val Ser Ile Ser Ser Cys Ile Asp Pro
                355                 360                 365

Leu Ile Tyr Tyr Tyr Ala Ser Ser Glu Cys Gln Arg Tyr Val Tyr Ser
                370                 375                 380

Ile Leu Cys Cys Lys Glu Ser Ser Asp Pro Ser Ser Tyr Asn Ser Ser
    385                 390                 395                 400

Gly Gln Leu Met Ala Ser Lys Met Asp Thr Cys Ser Ser Asn Leu Asn
                        405                 410                 415

Asn Ser Ile Tyr Lys Lys Leu Leu Thr
                420                 425
```

(2) INFORMATION FOR SEQ ID NO:58:

(i) SEQUENCE CHARACTERISTICS:
        (A) LENGTH: 80 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:58:

```
    Met Phe Lys Ser Val Val Tyr Ser Ile Leu Ala Ala Ser Leu Ala Asn
    1               5                   10                  15

Ala Met Arg Tyr Thr Ala Cys Thr Glu Ser Gly Gln Asn Gln Cys Ile
                20                  25                  30

Cys Glu Gly Asn Asp Val Cys Gly Gln Gly Arg Asn Cys Gln Phe Asp
                35                  40                  45

Ser Ser Gly Lys Lys Cys Val Glu Gly Glu Gly Thr Arg Lys Pro Gln
                50                  55                  60

Asn Glu Gly Gln His Asp Phe Asp Pro Ile Pro Glu Glu Tyr Leu Ser
    65                  70                  75                  80
```

(2) INFORMATION FOR SEQ ID NO:59:

(i) SEQUENCE CHARACTERISTICS:
        (A) LENGTH: 136 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:59:

Met Ile Lys Leu Ala Ile Leu Leu Leu Phe Thr Val Ala Ile Val Arg

```
            1               5                  10                  15
      Cys Gln Gly Pro Phe Gly Pro Gly Cys Glu Glu Ala Gly Cys Pro Glu
                      20                  25                  30

Gly Ser Ala Cys Asn Ile Ile Thr Asp Arg Cys Thr Cys Ser Gly Val
                      35                  40                  45

Arg Cys Arg Met His Cys Pro His Gly Phe Gln Arg Ser Arg Tyr Gly
              50                  55                  60

Cys Glu Phe Cys Lys Cys Arg Leu Glu Pro Met Lys Ala Thr Cys Asp
      65                  70                  75                  80

Ile Ser Glu Cys Pro Glu Gly Met Met Cys Ser Arg Leu Thr Asn Lys
                      85                  90                  95

Cys Asp Cys Lys Ile Asp Ile Asn Cys Arg Lys Thr Cys Pro Asn Gly
                      100                 105                 110

Leu Lys Arg Asp Lys Leu Gly Cys Glu Tyr Cys Glu Cys Arg Pro Lys
                      115                 120                 125

Arg Lys Leu Ile Pro Arg Leu Ser
                      130                 135
```

(2) INFORMATION FOR SEQ ID NO:60:

(i) SEQUENCE CHARACTERISTICS:
      (A) LENGTH: 60 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:60:

```
      Tyr Asn Arg Leu Cys Ile Lys Pro Arg Asp Trp Ile Asp Glu Cys Asp
      1               5                   10                  15

Ser Asn Glu Gly Gly Glu Arg Ala Tyr Phe Arg Asn Gly Lys Gly Gly
                      20                  25                  30

Cys Asp Ser Phe Trp Ile Cys Pro Glu Asp His Thr Gly Ala Asp Tyr
                      35                  40                  45

Tyr Ser Ser Tyr Arg Asp Cys Phe Asn Ala Cys Ile
          50                  55                  60
```